(12) United States Patent
Akselrod et al.

(10) Patent No.: US 8,969,790 B1
(45) Date of Patent: Mar. 3, 2015

(54) METHOD AND APPARATUS FOR RADIATION DOSIMETRY UTILIZING FLUORESCENT IMAGING WITH PRECISION CORRECTION

(71) Applicant: Landauer, Inc., Glenwood, IL (US)

(72) Inventors: Mark S. Akselrod, Stillwater, OK (US); James Bartz, Stillwater, OK (US); Fujian Ding, Wappingers Falls, NY (US); Vasiliy V. Fomenko, Stillwater, OK (US)

(73) Assignee: Landauer, Inc., Glenwood, IL (US)

( * ) Notice: Subject to any disclaimer, the term of this patent is extended or adjusted under 35 U.S.C. 154(b) by 0 days.

(21) Appl. No.: 14/173,890

(22) Filed: Feb. 6, 2014

Related U.S. Application Data

(60) Provisional application No. 61/880,491, filed on Sep. 20, 2013.

(51) Int. Cl.
  *G01J 1/58* (2006.01)
  *G01T 1/10* (2006.01)
  *G01N 23/22* (2006.01)

(52) U.S. Cl.
  CPC . *G01T 1/10* (2013.01); *G01N 23/22* (2013.01)
  USPC .............. 250/252.1; 250/483.1; 250/484.4; 250/484.5; 250/484.2

(58) Field of Classification Search
  USPC .......... 250/252.1, 361 R, 362, 363.01, 483.1, 250/484.2, 484.4, 484.5
  See application file for complete search history.

(56) References Cited

U.S. PATENT DOCUMENTS

| | | | |
|---|---|---|---|
| 5,731,590 A * | 3/1998 | Miller | 250/484.5 |
| 6,127,685 A | 10/2000 | Yoder et al. | |
| 6,198,108 B1 | 3/2001 | Schweitzer et al. | |
| 6,846,434 B2 | 1/2005 | Akselrod | |
| 7,098,470 B2 * | 8/2006 | Akselrod et al. | 250/581 |
| 7,141,804 B1 | 11/2006 | Akselrod et al. | |

(Continued)

FOREIGN PATENT DOCUMENTS

WO 2012035502 A2 3/2012

OTHER PUBLICATIONS

Akselrod M.S. and Sykora G.J., "Fluorescent Nuclear Track Detector technology—a new way to do passive solid state dosimetry," Radiat. Meas., 46 1671-1679 (2011).

(Continued)

*Primary Examiner* — David Porta
*Assistant Examiner* — Mamadou Faye
(74) *Attorney, Agent, or Firm* — Alchemy-Partner, PC

(57) ABSTRACT

A method comprising the following steps: (a) adjusting a radiation dose measurement for a fluorescent nuclear track detector based on a plurality of fluorescence contrast images for the fluorescent nuclear track detector to thereby produce a calibrated radiation dose measurement, and (b) displaying the calibrated radiation dose measurement to a user and/or saving the calibrated radiation dose measurement to a storage medium, wherein the fluorescent nuclear track detector comprises a luminescent material, wherein the radiation dose measurement is based on one or more fluorescent light measurements produced by fluorescent imaging of the fluorescent nuclear track detector using excitation light from a laser having a first wavelength, and wherein the plurality of fluorescence contrast images are produced by illuminating the fluorescent nuclear track detector with excitation light having a second wavelength.

18 Claims, 14 Drawing Sheets

(56) References Cited

U.S. PATENT DOCUMENTS

| | | | |
|---|---|---|---|
| 7,902,525 | B2 | 3/2011 | Akselrod et al. |
| 7,943,911 | B2 | 5/2011 | Akselrod et al. |
| 7,964,854 | B2 | 6/2011 | Akselrod et al. |
| 2003/0220549 | A1* | 11/2003 | Liu et al. ............... 600/317 |
| 2010/0102249 | A1* | 4/2010 | Akselrod et al. .......... 250/459.1 |
| 2011/0042580 | A1* | 2/2011 | Wilson et al. ............ 250/458.1 |
| 2012/0018652 | A1 | 1/2012 | Yoder et al. |
| 2013/0341514 | A1* | 12/2013 | Akselrod et al. ............ 250/362 |

OTHER PUBLICATIONS

Akselrod, M.S., Fomenko, V.V., Bartz, J.A., Haslett, T.L., "Commercial neutron dosimetry system based on fluorescent nuclear track detector technology," Rad. Prot. Dosim. (2013).

Sykora, G.J. and Akselrod, M.S., "Spatial frequency analysis of fluorescent nuclear track detectors irradiated in mixed neutron-photon fields," Radiat. Meas., 45, (10) 1197-1200, (2010).

Sykora, G. J. and Akselrod, M. S., "Novel fluorescent nuclear track detector technology for mixed neutron-gamma fields, Radiation Measurements.," Radiat. Meas. 45 (3-6), 594-598 (2010).

Sykora, G. J. and Akselrod, M. S., "Photoluminescence study of photochromically and radiochromically transformed Al2O3:C,Mg crystals used for fluorescent nuclear track detectors," Radiat. Meas. 45 (3-6) 631-634 (2010).

Sykora, G.J., Akselrod, M.S., Vanhavere, F., Performance of Fluorescence Nuclear Track Detectors in Monoenergetic and Broad Spectrum Neutron Fields. Radiat. Meas. 44, 988-991 (2009).

Sykora, G.J., Salasky, M., and Akselrod, M.S., "Properties of novel fluorescent nuclear track detectors for use in passive neutron dosimetry," Radiat. Meas. 43, 1017-1023 (2008).

Benton, E.V. Oswald, R.A. Frank, A.L. Wheeler, R.V., "Proton-recoil neutron dosimeter for personnel monitoring," Health Phys. 40, 801-809 (1981).

Benton, E.V., Ogura, K., Frank, A.L., Atallah, T.M. and Rowe, V., "Response of different types of CR-39 to energetic ions," Nuclear Tracks 12, 79-82 (1986).

Sykora, J., Akselrod, M.S., Benton, E.R. and Yasuda, N., "Spectroscopic properties of novel fluorescent nuclear track detectors for high and low LET charged particles.," Radiat. Meas. 43, 422-426 (2008).

Bartz, J.A., Zeissler, C.J., Fomenko, V.V., Akselrod, M.S., "An imaging spectrometer based on high resolution microscopy of fluorescent aluminum oxide crystal detectors," Radiat. Meas., In Press, Corrected Proof, Available online Feb. 27, 2013.

Niklas, M., Melzig, C., Abdollahi, A., Bartz, J., Akselrod, M.S., Debus, J., Jäkel, O. and Greilich, S. "Spatial correlation between traversal and cellular response in ion radiotherapy—Towards single track spectroscopy," Radiat. Meas., In Press, Corrected Proof, Available online Feb. 21, 2013.

ANSI N13.11-2009 American National Standard for Dosimetry—Personnel Dosimetry Performance—Criteria for Testing (2009).

ISO-21909-1, Passive neutron dosimetry systems—Part 1: Performance and test requirements for personal dosimetry. Apr. 2013 (draft).

Bartz, J.A. Sykora, G.J. Bräuer-Krisch, and E. Akselrod, M.S., "Imaging and dosimetry of synchrotron microbeam with aluminum oxide fluorescent detectors," Radiat. Meas., 46 1936-1939 (2011).

Botter-Jensen, L., et al., "Optically Stimulated Luminescence Dosimetry," Elsevier, 2003.

Klemic, G., et al., "External Dosimetry in the Aftermath of a Radiological Terrorist Event," Radiation Protection Dosimetry, vol. 120, No. 1-4, pp. 242-249, 2006.

Akselrod, M.S., et al., "Preparation and Properties of Al2O3:C," Radiation Protection Dosimetry, vol. 47, No. 1-4, pp. 159-164, 1993.

Akselrod, M.S., et al., "Optically Stimulated Luminescence of Al2O3," Radiation Measurements, vol. 29, No. 3-4, pp. 391-399, 1998.

Akselrod, et al., "Fluorescent Nuclear Track Detector Technology—A New Way to Do Passive Solid State Dosimetry," Radiation Measurements, vol. 46, pp. 1671-1679, Jun. 7, 2011.

* cited by examiner

METHOD AND APPARATUS FOR RADIATION DOSIMETRY UTILIZING FLUORESCENT IMAGING WITH PRECISION CORRECTION

CROSS-REFERENCE TO RELATED APPLICATIONS

This application claims benefit of priority to U.S. Provisional Patent Application No. 61/880,491, entitled "METHOD AND APPARATUS FOR RADIATION DOSIMETRY UTILIZING FLUORESCENT IMAGING WITH PRECISION CORRECTION," filed Sep. 20, 2013 which is incorporated by reference in its entirety.

BACKGROUND

1. Field of the Invention

The present invention relates to dosimetric radiation measurements using a fluorescent nuclear track detector (FNTD).

2. Related Art

There are various deficiencies in existing techniques for measuring radiation absorption in fluorescent nuclear track detectors.

SUMMARY

According to a first broad aspect, the present invention provides a method comprising the following steps: (a) adjusting a radiation dose measurement for a fluorescent nuclear track detector based on a plurality of fluorescence contrast images for the fluorescent nuclear track detector to thereby produce a calibrated radiation dose measurement, and (b) displaying the calibrated radiation dose measurement to a user and/or saving the calibrated radiation dose measurement to a storage medium, wherein the fluorescent nuclear track detector comprises a luminescent material, wherein the radiation dose measurement is based on one or more fluorescent light measurements produced by fluorescent imaging of the fluorescent nuclear track detector using excitation light from a laser having a first wavelength, and wherein the plurality of fluorescence contrast images are produced by illuminating the fluorescent nuclear track detector with excitation light having a second wavelength.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Definitions

Figure 1:
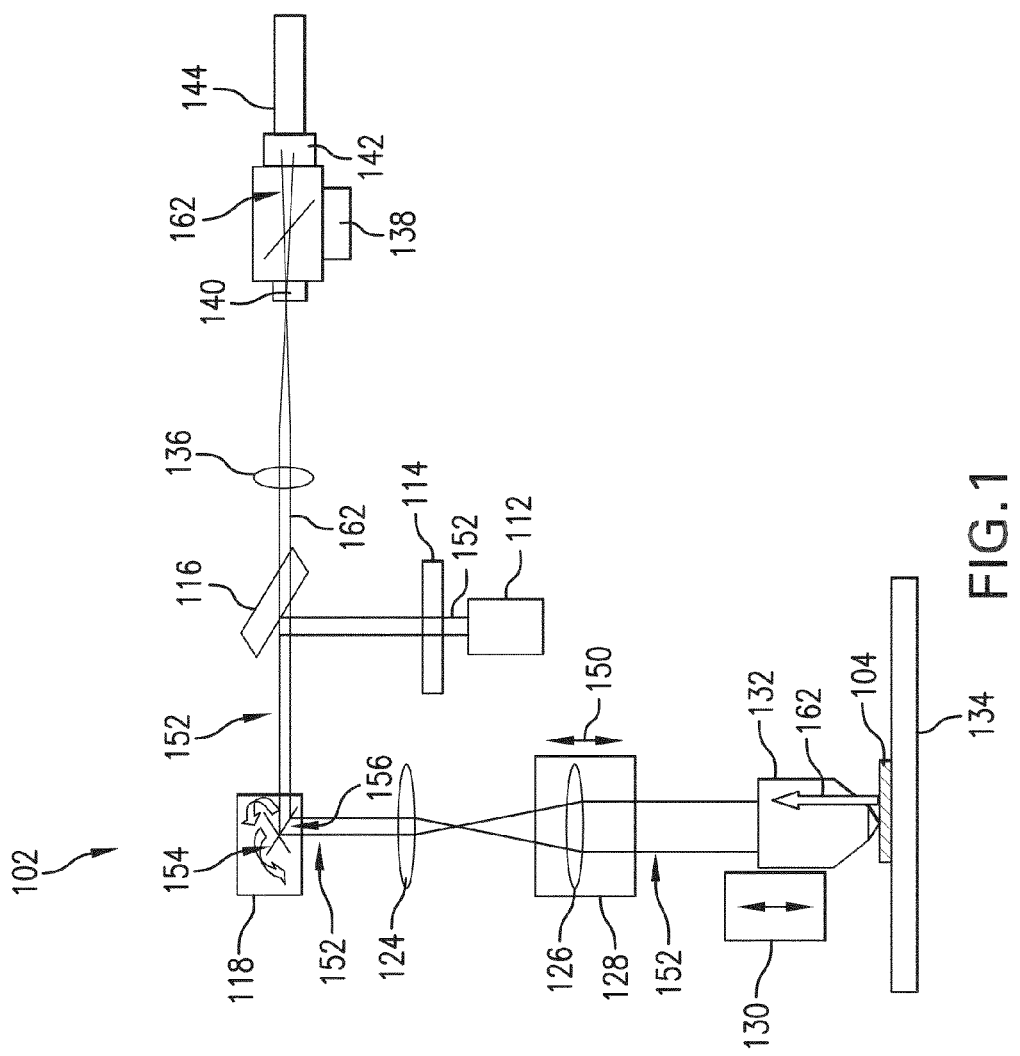
FIG. 1 is schematic diagram of a fluorescent nuclear track detector (FNTD) reader.

Where the definition of terms departs from the commonly used meaning of the term, applicant intends to utilize the definitions provided below, unless specifically indicated. For purposes of the present invention, directional terms such as "top", "bottom", "upper", "lower", "above", "below", "left", "right", "horizontal", "vertical", "upward", "downward", etc. are merely used for convenience in describing the various embodiments of the present invention.

For purposes of the present invention, a value or property is "based" on a particular value, property, the satisfaction of a condition, or other factor, if that value is derived by performing a mathematical calculation or logical decision using that value, property or other factor. For example, a dosimetry detection device used with the method of the present invention may be calibrated based on the spatial distribution of fluorescence measured by the device when the device is used to measure the fluorescence of a luminescent material exposed to heavy charged particle of known type, energy and angle of incidence.

For purposes of the present invention, the term "analog mode" refers to average intensity or power spectrum integral of one of more images (or part of the image) obtained in red-stimulated fluorescence contrast using FNTD detector and laser scanning confocal fluorescent microscopy technique.

For purposes of the present invention, the term "bleached detector" refers to a radiation detector, such as an FNTD that is bleached by a process such as illuminating and scanning the detector with the high intensity laser light produced for example by a nitrogen laser or by solid state laser and generating short (for example several nanoseconds) laser pulses in the wavelength range 330-355 nm.

For purposes of the present invention, the term "color center" refers to the conventional meaning of the term "color center", i.e. a point defect in a crystal lattice that gives rise to an optical absorption in a crystal and upon light excitation produces a photon of luminescence. A color center, an impurity or an intrinsic defect in a crystalline material creates an unstable species. An electron localized on this unstable species or defect performs a quantum transition to an excited state by absorbing a photon of light and performs a quantum transition back to a ground state by emitting a photon of luminescence.

For purposes of the present invention, the term "confocal detection" refers generally to the descanned detection of fluorescent light where the light emitted from the focal plane of an object (crystal) and from the planes located above and below the latter reaches a dichroic beam splitter or mirror. This dichroic beam splitter/mirror separates the fluorescent light from the excitation light, with the fluorescent light being subsequently focused on a diaphragm (confocal diaphragm/pinhole) located precisely in a plane conjugate to the focal plane inside the object. The optical resolution of the microscope may be adjusted by varying the size of the diaphragm. Another dichroic blocking filter which again suppresses the excitation radiation is located in front or behind the diaphragm. After passing the blocking filter, the fluorescent light is measured by a photodetector. A typical confocal detection scheme involves the arrangement of a scanning confocal microscope in which a small aperture is installed in front of a photodetector in the position of the secondary focus of the imaging system and where the laser beam reflected from the medium or the laser induced fluorescence light from the medium is collected by the objective lens and is imaged on the aperture using a dichroic beam splitter, mirrors, lenses and/or other optical components.

For purposes of the present invention, the term "computer" refers to any type of computer or other device that implements software including an individual computer such as a personal computer, laptop computer, tablet computer, mainframe computer, mini-computer, microprocessor, field-programmable gate array (FPGA), etc. A computer also refers to electronic devices such as a smartphone, an eBook reader, a cell phone, a television, a handheld electronic game console, a videogame console, a compressed audio or video player such as an MP3 player, a Blu-ray player, a DVD player, etc. In addition, the term "computer" refers to any type of network of computers, such as a network of computers in a business, a computer bank, the Cloud, the Internet, etc.

For purposes of the present invention, the term "converter of radiation" or just "converter" refers to a layer of the material used to convert one type of radiation into another. For example hydrogen-containing material like polyethylene is used to convert non-ionizing neutron radiation into recoil or knockout protons which are capable of performing ionization in luminescent detector material. Another example of a converter of radiation is lithium fluoride (LiF) that naturally contains $^6$Li that has a high capture cross-section for moderated and thermal neutrons with alpha particles and tritium ions as nuclear reaction products that ionize the detector material and produce fluorescent tracks. Yet another well-known type of thermal neutron converter is any material containing isotope of $^{10}$B-like boron oxide and boron carbide. For maintaining electron equilibrium when detecting X-rays or gamma photons while discriminating against neutrons, converters are made of non-hydrogen-containing material like fluorinated plastics such as polytetrafluoroethylene (PTFE).

For purposes of the present invention, the term "crystalline material" refers to the conventional meaning of the term "crystalline material", i.e. any material that has orderly or periodic arrangement of atoms in its structure.

For purposes of the present invention, the term "defect" refers to the conventional meaning of the term "defect" with respect to the lattice of a crystal, i.e. a vacancy, interstitial, impurity atom or any other imperfection in a lattice of a crystal.

For purposes of the present invention, the term "diffuse reflection contrast" refers to an image of an object (crystal) formed by diffuse light reflected by the object. For example, the term "near-infrared (NIR) diffuse reflection contrast" refers to an image of an object (FNTD crystal) formed by diffuse NIR light reflected by the object.

For purposes of the present invention, the term "diffuse reflection mode of imaging" refers to imaging of the object (crystal) at the same wavelength as illumination wavelength. No light separation between excitation and emission light is required. It refers to a mode of operation of a radiation detector wherein light reflected by an FNTD crystal is imaged by the camera (imaging device). In one embodiment of the present invention, the slight reflected by an FNTD crystal is detected by the imaging (CMOS or CCD) camera under near-infrared (NIR) illumination.

For purposes of the present invention, the term "fluorescence" refers to the conventional meaning of the term "fluorescence", i.e., a type of luminescence in which an atom, molecule, etc., emits visible radiation during quantum transition from a higher to a lower electronic state and where the time interval between absorption and emission of energy is typically extremely short (e.g., $10^{-10}$ to $10^{-1}$ seconds).

For purposes of the present invention, the term "fluorescent color centers" refers to color centers that are able to fluoresce under light stimulation.

For purposes of the present invention, the term "fluorescence contrast" refers to an image of an object (crystal) formed by fluorescent light emitted by the object. For example, the term "green fluorescent contrast" refers to an image of an object formed by green fluorescent light emitted by the object.

For purposes of the present invention, the term "hardware and/or software" refers to a device that may be implemented by digital software, digital hardware, or a combination of both digital hardware and digital software.

For purposes of the present invention, the term "ionizing radiation" refers to any particulate or electromagnetic radiation that is capable of dissociating atoms into ions and electrons. The present invention may be used to determine doses of both directly ionizing radiation and indirectly ionizing radiation.

For purposes of the present invention, the term "irradiation" refers to the conventional meaning of the term "irradiation", i.e., exposure to high energy charge particles, e.g. electrons, protons, alpha particles, etc., or electromagnetic radiation of wave-lengths shorter than those of visible light, e.g., gamma rays, x-ray, ultraviolet, etc.

For purposes of the present invention, term the "microprocessor" refers to a computer processor contained on an integrated circuit chip, such a processor may also include memory and associated circuits. A microprocessor may further comprise programmed instructions to execute or control selected functions, computational methods, switching, etc. Microprocessors and associated devices are commercially available from a number of sources, including, but not limited to, Cypress Semiconductor Corporation, IBM Corporation, Applied Microsystems Corporation, Intel Corporation, Microchip Technology, etc.

For purposes of the present invention, the term "near-infrared (NIR)" refers to light having a wavelength from about 700 nm to about 2500 nm.

For purposes of the present invention, the term "OSLM" refers to an optically stimulated luminescence (OSL) material, i.e., a material whose exposure to radiation (directly, indirectly or low-penetrating) may be determined using optically stimulated luminescence techniques. An $Al_2O_3$ material, such as an $Al_2O_3$:C,Mg, is an example of an OSLM. The amount of radiation exposure that an $Al_2O_3$ material has received may be measured by stimulating the $Al_2O_3$ material with green light from either a laser or light emitting diode source. The resulting blue light emitted from the $Al_2O_3$ is proportional to the amount of radiation exposure and the intensity of stimulation light. Both high and low-energy photons and beta particles can be measured with this technique. For more information on OSL materials and systems, see, U.S. Pat. No. 5,731,590 issued to Miller; U.S. Pat. No. 6,846,434 issued to Akselrod; U.S. Pat. No. 6,198,108 issued to Schweitzer et al.; U.S. Pat. No. 6,127,685 issued to Yoder et al.; U.S. patent application Ser. No. 10/768,094 filed by Akselrod et al.; all of which are incorporated herein by reference in their entireties. See also Optically Stimulated Luminescence Dosimetry, Lars Botter-Jensen et al., Elesevier (2003); Klemic, G., Bailey, P., Miller, K., Monetti, M. External radiation dosimetry in the aftermath of radiological terrorist event, Rad. Prot. Dosim., 120 (1-4): 242-249 (2006); Akselrod, M. S., Kortov, V. S., and Gorelova, E. A., Preparation and properties of $Al_2O_3$:C, Radiat. Prot. Dosim. 47, 159-164 (1993); and Akselrod, M. S., Lucas, A. C., Polf, J. C., McKeever, S. W. S. Optically stimulated luminescence of $Al_2O_3$:C, Radiation Measurements, 29, (3-4), 391-399 (1998), all of which are incorporated herein by reference in their entireties.

For purposes of the present invention, the term "non-transitory storage medium" refers to any storage medium that stores bits of information in a non-transitory manner.

For purposes of the present invention, the term "OSL reader" refers to a device that produces stimulation light that stimulates an OSLM in an OSL sensor to emit luminescent light. Under a specified stimulation regime (continuous stimulation, reading wavelength and intensity, and pulsed stimulation with various pulse durations, pulse frequency, pulse shape and time between pulses) the intensity of the emitted light is proportional to the radiation exposure in a range from about 0.01 mGy (1 mrad) to over about 100 Gy (10,000 rads).

For purposes of the present invention, the term "Power Spectrum Integral (PSI)" refers to an integral of two-dimensional spatial frequency spectrum of the image obtained by Discrete Fast Fourier Transform. PSI is a dosimetric parameter that is directly proportional to the absorbed dose of radiation, see U.S. Pat. No. 7,902,525 to Akselrod et al., U.S. Pat. No. 7,943,911 to Akselrod et al., and U.S. Pat. No. 7,964,854 to Akselrod et al., the entire contents and disclosures of which are incorporated herein by reference.

For purposes of the present invention, the term "processor" refers to a device capable of, for example, executing instructions, implementing logic, calculating and storing values, etc. Exemplary processors may include application specific integrated circuits (ASIC), central processing units, microprocessors, such as, for example, microprocessors commercially available from Intel and AMD, etc.

For purposes of the present invention, the term "radiation dose" refers to the value of the radiation dose for a particular type of radiation to which a radiation detector has been exposed.

For purposes of the present invention, the term "radiation dosimetry" refers to the conventional meaning of the term "radiation dosimetry", i.e., the measurement of the amount of radiation dose absorbed in a material, an object or the body of an individual.

For purposes of the present invention, the term "red fluorescence" and the term "red fluorescent" refers to fluorescence in the range of 680 to 850 nm. "Red fluorescence" may refer to light that is red or near-infrared. In one embodiment of the present invention, "red fluorescence" is caused by stimulating a luminescent material with red laser light.

For purposes of the present invention, the term the term "storage medium" refers to any form of storage that may be used to store bits of information. Examples of storage media include both volatile and non-volatile memories such as MRRAM, MRRAM, ERAM, flash memory, RFID tags, floppy disks, Zip™ disks, CD-ROM, CD-R, CD-RW, DVD, DVD-R, flash memory, hard disks, optical disks, etc.

For purposes of the present invention, the term "track" refers to latent or visible image of a particle trajectory penetrating the medium.

For purposes of the present invention, the term "trap" refers to an electron trap or a hole trap. A trap is a structural defect in a crystal lattice able to create a localized electronic state and capable of capturing a free electron or a hole from the conduction or valence band of the crystalline material.

For purposes of the present invention, the term "visual display device," the term "visual display apparatus" and the term "visual display" refer to any type of visual display device or apparatus such as a an LCD screen, touch-screen, a CRT monitor, LEDs, a projected display, a printer for printing out an image such as a picture and/or text, etc. A visual display device may be a part of another device such as a computer monitor, television, projector, cell phone, smartphone, laptop computer, tablet computer, handheld music and/or video player, personal data assistant (PDA), handheld game player, head mounted display, a heads-up display (HUD), a global positioning system (GPS) receiver, automotive navigation system, dashboard, watch, etc.

Description

A fluorescent nuclear track detector (FNTD) is a passive integrating type of radiation detector that has been described comprehensively in the literature (see References 1, 2 and 3). FNTDs are made of sapphire single crystals doped with carbon and magnesium ($Al_2O_3$:C,Mg). The FNTD crystal contains aggregate oxygen vacancy defects that have good temperature (~600° C.) and environmental stability, no ambient light sensitivity or thermal fading. This type of radiation detector is immune to electromagnetic interference and can measure doses at extremely high dose rates (~$10^8$ Gy/s) in pure and mixed neutron and photon fields (References 1, 2, 3, 4, 5, 6, 7 and 8). FNTDs can be read multiple times nondestructively and are reusable after thermal annealing and/or optical bleaching. Additional attractive features of the $Al_2O_3$:C,Mg FNTD include the superior spatial resolution of detector readout, a wider range of Liner Energy Transfer (LET) sensitivity to heavy charged particles compared to conventional CR-39 plastic nuclear track detectors and no need for long post-irradiation chemical etching in NaOH (Reference 9) as in the case of CR-39. As a passive detector, FNTDs do not require wires, electronics or batteries during irradiation. To-date, FNTD technology has achieved a sufficient level of maturity to be successfully used in research and in commercial applications. The applicability of FNTDs was demonstrated in high resolution synchrotron microbeam imaging (Reference 10), heavy charged particle LET spectroscopy (Reference 11), alpha particle imaging spectrometry using 3D track reconstruction (Reference 12), and radiobiology experiments on co-localization between DNA double-strand brakes in live cells and tracks of high energy carbon ions used in radiotherapy (Reference 13). Recently, a commercial dosimetry system utilizing FNTD technology has been released (Reference 2). The commercial system has been shown to comply with the US ANSI N13.11-2009 (Reference 14) and the draft of ISO-21909-1 (Reference 15) standards for measurements of mixed neutron-photon fields with different ratios of neutrons ($^{241}$AmBe, bare and moderated $^{252}$Cf) and photons ($^{137}$Cs and X-rays).

FNTD technology provides a unique opportunity to record the optical fluorescent image of the energy deposition caused by ionizing radiation. The spatial variation of the radiation-induced fluorescence in the crystal caused by the ionizing radiation can be assessed through confocal laser scanning fluorescent imaging (References 1, 2, 3, 4 and 5). This high resolution imaging capability provides two modes in which the FNTD technology can operate: the "digital" or track counting mode and the "analog" mode (References 1, 2, 3 and 4). In the track counting mode, useful up to ~50 mSv of total neutron plus photon dose, fluorescent tracks are created by heavy charged particles or recoil protons, resulting from neutron interactions with converters (polyethylene or $^6$Li-containing materials) covering FNTDs. In the case of fast-neutron irradiation, recoil protons are produced through neutron scattering in polyethylene, the material with the highest concentration of hydrogen among solids. Moderated and thermal neutrons are efficiently absorbed by $^6$Li nuclei, resulting in nuclear reaction which produces alpha particles and tritons.

In track-counting mode, the FNTD can be regarded as a "binary" detector, i.e., the track is either present or not. Therefore, individual-detector calibration or sensitivity correction is not required even when crystals have different concentrations of radiation-sensitive color centers. The "analog" mode utilizes either the average "red fluorescence" intensity of the images ($F_{red}$) or the image power-spectrum integral (PSI) as a metric for the dose (References 1, 3 and 4). In the description and examples below, the results obtained with the PSI metric are used, since it has been found by the inventors that the PSI works reliably in a wider dose range compared to the average "red fluorescence" image intensity excited by red light. Similar results were obtained for both PSI and average "red fluorescence" image intensity used as a dosimetric parameter. In mixed neutron-photon fields with doses higher than 50 mSv, the fluorescent tracks created by heavy charged particles or delta electrons start coalescing, and the track density becomes too high for reliable track counting and analog image processing mode is used.

The analog method, not reliant on identification and counting of individual tracks, is required for measuring doses higher than 50 mSv. However, the magnitude of the power spectrum integral, the analog parameter developed for high-dose neutron and photon measurements, depends not only on the irradiation dose, but also on the color center concentration in each FNTD crystal. Since color center concentration varies from detector to detector, precise dose estimation requires an estimation of the color-center concentration in each detector. A method for measuring the color center concentration and thus calibrating the sensitivity for each detector can be rationalized from inspecting the excitation-emission spectrum of photoluminescence of FNTD $Al_2O_3$:C,Mg crystals. The spectroscopic features most relevant to the crystal coloration and the radiation sensitivity are the excitation-emission bands peaked at 435/520 nm and assigned to $F_2^{2+}$ (2Mg) and the band at 620/750 nm, assigned to $F_2^+$ (2Mg) (References 1 and 5). It has been determined that the $F_2^{2+}$ (2Mg) centers responsible for green coloration of the crystals are electron traps and have the highest concentration in annealed (or erased state of the crystalline detector) (References 1 and 5). These color centers undergo radiochromic transformation into $F_2^+$ (2Mg) centers as a result of electron capture during irradiation (Reference 5). Thus, the intensity of the $F_2^{2+}$ (2Mg) band, further referred to as "green fluorescence" ($F_{green}$), characterizes the initial coloration of the crystal and the sensitivity of this crystal to radiation, while the $F_2^+$ (2Mg) band, further referred to as "red fluorescence", carries the dosimetric information. In one embodiment of the present invention, the concentration of color centers may be determined by exciting the $F_2^{2+}$ (2Mg) color centers with blue light around 440 nm and measuring the resulting green fluorescence centered at 520 nm.

The intensity of green fluorescence, collected from an FNTD, is affected by diffuse reflection of both excitation light and fluorescent emission that occurs at the interfaces of the detector. In one embodiment of the present invention, only one side of FNTD crystals is polished to optical quality. The other side of the crystal is only lapped and thus, the roughness of the lapped surface may vary considerably from crystal to crystal. The diffuse reflection (scattering) on the unpolished surface ultimately affects the efficiency with which green fluorescence is collected. Thus, a precise, reproducible measurement of the green fluorescence intensity requires an estimation of the degree of diffuse reflection incurred on the lapped surface of the detector. The diffuse reflection can be characterized by illuminating the FNTD with light that is not optically active, i.e. does not make the crystal fluoresce and collecting the scattered light in diffuse reflection geometry.

In determining the absorbed radiation dose for an FNTD, the average Power Spectrum Integral (PSI) parameter is used as an analog parameter that is proportional to the absorbed dose of radiation as described in U.S. Pat. No. 7,902,525 (the PSI parameter is referred to as the "spatial frequency power spectrum integral in U.S. Pat. No. 7,902,525), the entire contents and disclosure of which are incorporated herein by reference. PSI obtained from the FNTD area behind the polyethylene (PE) or Li-glass converters is proportional to both photon dose and neutron dose, whereas PSI parameter obtained from FNTD area behind the PTFE converter is proportional only to the photon dose. The neutron dose is calculated by subtracting those two signals after corresponding sensitivity corrections. The sensitivity coefficient of the analog PSI and red fluorescence intensity can be different in value for neutron and photons and may also depend on the energy of both neutrons and photons.

Another analog parameter utilized to determine the radiation dose is average fluorescence intensity after the subtraction of the background signal using techniques such as those described in U.S. Pat. No. 7,098,470, the entire contents and disclosure of which are incorporated herein by reference. This parameter can be determined from processing of red fluorescent laser scanning confocal image. For example, this may be calculated as an average fluorescent intensity or a sum of image pixels from one or more images within defined region of interest of the detector.

It has now been determined that both the value of the PSI parameter and average red fluorescence intensity of irradiated detector are not only proportional to the absorbed dose but also depend on the color center concentration of each $Al_2O_3$: C,Mg crystalline detector. Currently, the concentration of radiation sensitive color centers is determined by techniques such as: (1) measuring optical absorption measurements at particular wavelengths corresponding to the color center of interest using a spectrophotometer and (2) measuring intensity of fluorescence under excitation with light corresponding to the optical absorption band of said color centers. But spectrophotometers used in technique (1) are complex, bulky and expensive. Also technique (1) requires optically transparent polished crystals, even though commercial FNTD crystals are usually polished only on one side. With respect to technique (2), in at least some embodiments, the method of the present invention is simpler, quicker and can be combined with imaging of engraved ID.

It has been established that the FNTD technology can be used successfully for high dose measurements through the use of analog parameters, the average fluorescence intensity or the power spectrum integral of confocal "red fluorescent" images. The analog mode of image processing is particularly useful at high doses when the use of track-counting mode is limited by track coalescence. However, the use of analog mode requires sensitivity correction on color center concentration for each FNTD. In one embodiment, the present invention provides a method for calibrating the sensitivities of individual FNTDs through an assessment of the color center concentration in individual FNTDs using additional dual mode green fluorescence and diffuse reflection IR imaging. In at least some embodiments of the present invention, the sensitivity calibration does not require additional irradiation of the detector.

In one embodiment, the present invention provides a method of measuring radiation dose using fluorescent nuclear track detectors (FNTDs) in analog mode. The method may be applied for measurements of photons, neutrons and other types of directly and indirectly ionizing radiation.

In one embodiment, the method of the present invention provides improved accuracy and precision of measurements correcting fluorescent measurements obtained using the methods described U.S. Pat. No. 7,098,470, U.S. Pat. No. 7,141,804, U.S. Pat. No. 7,902,525, U.S. Pat. No. 7,943,911 and U.S. Pat. No. 7,964,854, the entire contents and disclosures of which are incorporated herein by reference. The fluorescent measurements are corrected by using measurements of green fluorescence and NIR scatter image of the same FNTD detectors and applying corrections according to an algorithm.

In one embodiment, the present invention provides a method for radiation dosimetry using Fluorescent Nuclear Track Detectors (FNTDs), which includes non-destructive, automatic sensitivity calibration for each individual FNTD. In one embodiment of the present invention, confocal laser scanning fluorescent imaging of FNTDs is combined with dual-color wide field imaging of the FNTD. The calibration is achieved by measuring the color center concentration in the detector through fluorescence imaging and reducing the effect of diffuse reflection on the lapped surface of the FNTD by imaging with near-infrared (NIR) light. In one embodiment of the present invention, dual-color imaging of FNTDs provides a good estimation of the detector sensitivity at high doses of photons and neutrons, where conventional track counting is impeded by track overlap.

In one embodiment, the present provides a method of radiation sensitivity determination for each FNTD in "analog mode" without actually performing individual pre- or post-irradiation calibration of each crystal. This prediction method is based on estimation of a radiation sensitive color center concentration in each crystal by measuring intensity of green fluorescence emitted by the crystal under blue light excitation. Additional correction of green fluorescence on intensity of scatter of each crystal (for example, in near-infrared light) provides further improvements of dose determination accuracy.

In one embodiment of the present invention, both, color center concentration measurements and scatter measurements may be performed either by integrating signal on a single element (single pixel) detector such as a photodiode, photomultiplier tube (PMT) or avalanche photodiode (APD), or by obtaining images from multi-pixel devices (CMOS or CCD cameras) in fluorescence and NIR diffuse reflection contrast. The multi-pixel camera approach has significant advantages, because obtaining the detector image provides the data on the crystal sensitivity and non-uniformity for the exact crystal location where the radiation-induced red laser scanning "red fluorescent" imaging is performed. Another advantage of a multi-pixel detector is the fast imaging of the whole detector. Thus, the dose determination time is essentially unaffected by the correction procedure.

In one embodiment, the present invention provides a method of obtaining an FNTD image in green fluorescence contrast under blue LED excitation and a diffuse reflection image under NIR LED illumination. Both images make it possible to obtain the engraved detector ID.

FIG. 1 shows a fluorescent nuclear track detector (FNTD) reader 102 that may be used to read an FNTD 104 according to one embodiment of the present invention. FNTD reader 102 includes a laser 112 with a collimator, a shutter 114, a dichroic mirror 116, an XY scanner 118, a front relay lens 124, a rear relay lens 126, a 1-D stepper stage 128, a Z-axis piezo positioner of the objective lens 130, an objective lens 132, XY stepper stages 134, and a light detection assembly comprising: a pinhole imaging lens 136, a photodiode 138, a confocal pinhole 140, a long-pass filter 142 and an avalanche photodiode 144. Red laser light 152 having a wavelength of 635 nm is emitted from laser 112, passes through shutter 114 and is reflected by dichroic mirror 116. Laser light 152 reflected by dichroic mirror 116 is in turn reflected by XY scanner 118 through front relay lens 124, rear relay lens 126 and objective lens 132 and onto FNTD 104. XY scanner may comprise a 2D MEMES scanner with one mirror scanning along two axes or 2D galvanometer scanner that includes two mirrors 154 and 156 that scan linearly along the x-axis and y-axis of stepper stages 134. 1-D stepper stage 128 controls the position of rear relay lens 126 in a z-axis perpendicular to the plane of XY stepper stages 134 as indicated by double-headed arrow 150. Z-axis piezo positioner 130 controls the position of objective lens 132 in the z-axis. XY stepper stages 134 may be moved in the XY plane to allow all of FNTDs 104 loaded on the reader tray to be read by FNTD reader 102. When FNTD 104 is exposed to laser light 152, FNTD emits fluorescent light 162 that travels through objective lens 132, rear relay lens 126, front relay lens 124 and is reflected by XY scanner 118, through dichroic mirror 116, through imaging lens 136, confocal pinhole 140, long-pass filter 142 and is detected by avalanche photodiode 144. Long-pass filter 142 is a 695 nm long-pass or similar in performance optical filter.

The FNTD reader shown in FIG. 1 is based on a confocal laser scanning microscope concept.

Figure 2:
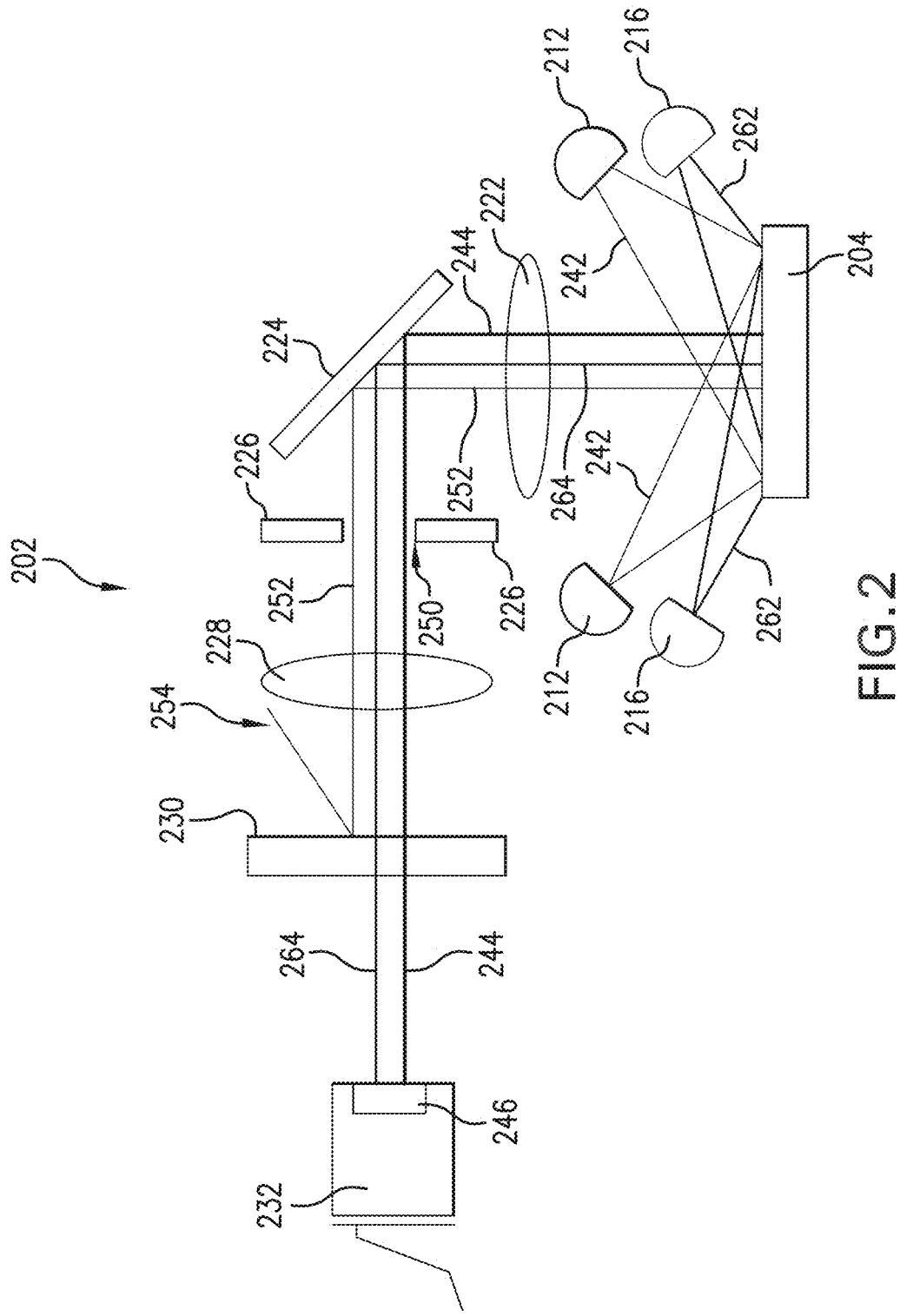
FIG. 2 is a schematic diagram of an imaging camera head according to one embodiment of the present invention.

FIG. 2 shows a schematic diagram of a method for obtaining green fluorescent contrast images of FNTDs and a method for obtaining near-infrared (NIR) diffuse reflection contrast images of FNTDs according to one embodiment of the present invention. FIG. 2 shows an imaging camera head 202 used to image an FNTD crystal 204. Imaging camera head includes blue LEDs 212, near-infrared (NIR) LEDs 216, an imaging lens 222, a mirror 224, an aperture 226, an imaging lens 228, yellow long-pass filter 230 and a CMOS camera 232. Blue LEDs 212 are turned on and illuminate FNTD crystal 204, positioned in the object plane of the camera optics, with blue excitation light 242. Blue excitation light 242 excites FNTD crystal 204 thereby causing FNTD crystal 204 to emit green fluorescent light 244. Green fluorescent light 244 is collected and imaged by imaging lenses 222 and 228 on a sensor 246 of CMOS camera 232. Although, only two blue LEDS 212 visible in FIG. 2, imaging camera head includes four blue LEDs 212 as indicating by the four beams of blue excitation light 242 shown in FIG. 2.

Green fluorescent light 244 passes through an opening 250 of aperture 226 and yellow long-pass filter 236. In contrast, stray blue excitation light 252 is absorbed or reflected by yellow long-pass filter 230, as indicated by arrow 254. After the image in green fluorescent contrast is acquired blue LEDs 212 are turned off and NIR LEDs 216 are turned on to illuminate FNTD crystal 204 with NIR light 262. Diffuse reflected NIR light 264 reflected from the FNTD crystal 204 is collected and imaged by imaging lenses 222 and 228 on a sensor 246 of the CMOS camera 232 in the same way as green fluorescent light 244 is imaged because diffuse reflected NIR light 262 can pass through yellow long-pass filter 230. Although, only two NIR LEDS 216 are visible in FIG. 2, imaging camera head includes four NIR LEDs 212 as indicating by the four beams of NIR light 262 shown in FIG. 2.

Although only two blue LEDs are shown in FIG. 2, an imaging camera head of the present invention may employ any number of blue LEDs. Although blue LEDS are shown in FIG. 2, depending on the type of FNTD crystal, other colors of LEDS may be used to provide stimulation light Although two NIR LEDs are shown in FIG. 2, an imaging camera head of the present invention may employ any number of NIR LEDs.

Figure 3:
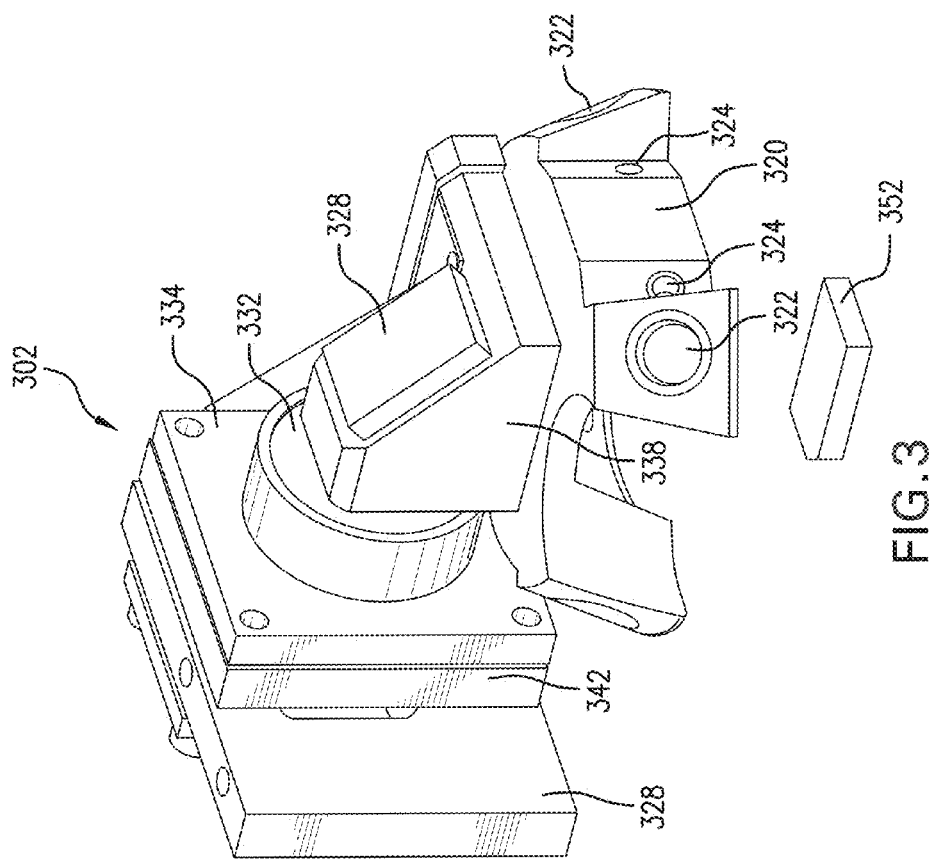
FIG. 3 is a perspective view of an imaging camera head according to one embodiment of the present invention.
Figure 4:
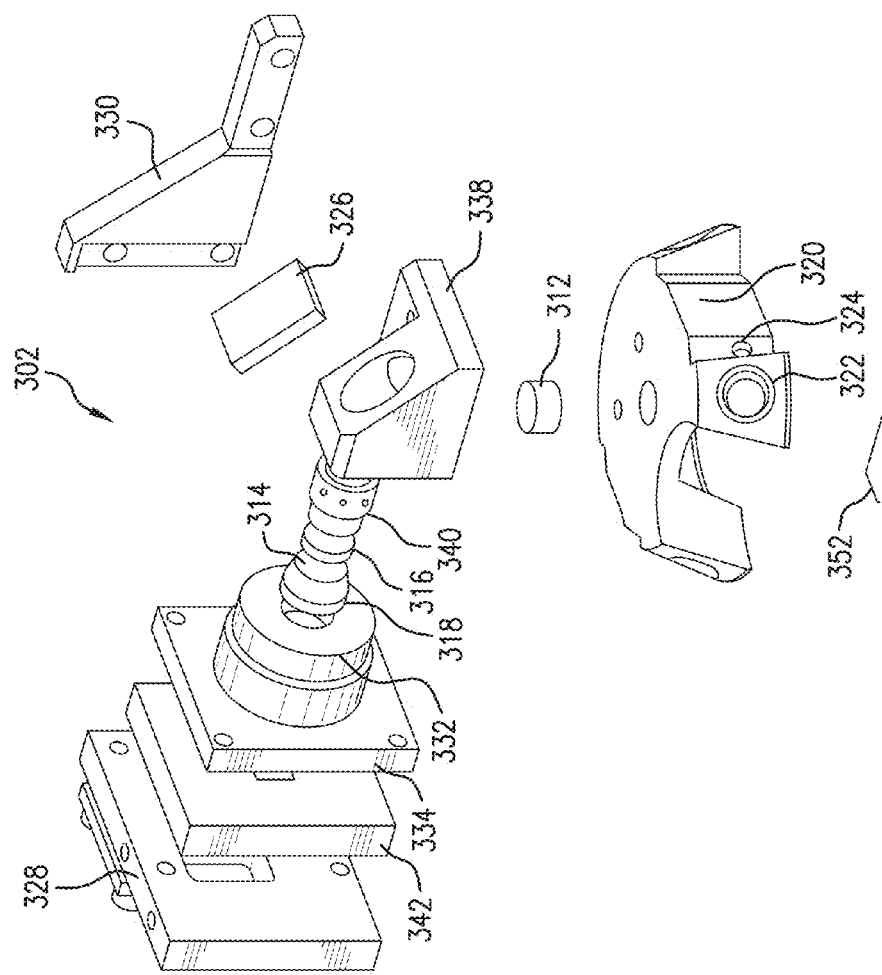
FIG. 4 is an exploded perspective view of the imaging camera head of FIG. 3.
Figure 5:
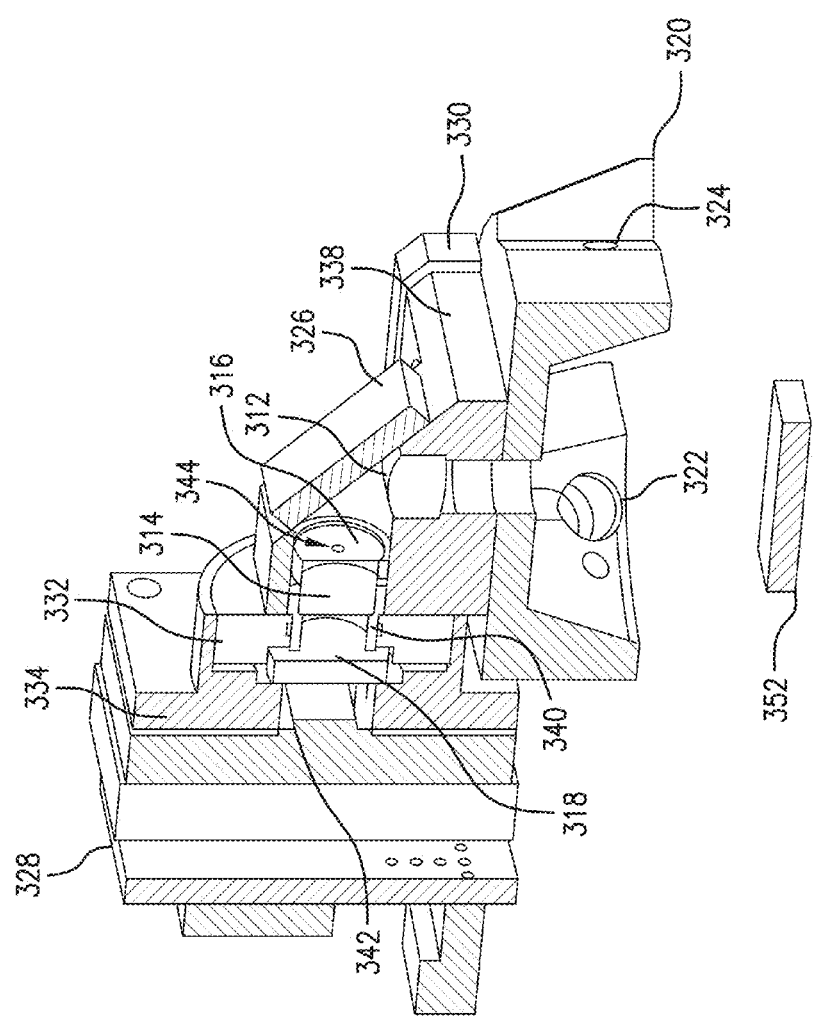
FIG. 5 is a cross-sectional perspective view of the imaging camera head of FIG. 3.

FIGS. 3, 4 and 5 show a camera head 302 that may be used for obtaining images of FNTDs in green fluorescent contrast and for obtaining images in near-infrared (NIR) diffuse reflection contrast according to one embodiment of the present invention. Camera head 302 is part of an FNTD reader (not shown) and may be designed to read sequentially two images of each FNTD crystal loaded on an FNTD reader tray (not shown). Camera head 302 includes an imaging lens 312, an imaging lens 314, an aperture 316, a long-pass filter 318, an LED housing 320 including blue LED openings 322 and NIR LED openings 324, a folding mirror 326, a camera bracket and interconnect board 328, a bracket 330, a retaining nut 332 for long-pass filter 318, a retaining nut housing 334 in which retaining nut 332 is rotatably mounted, a housing 338 for imaging lenses 312 and 314, a focus adjusting housing 340 for imaging lens 314, and a CMOS camera board 342. Aperture 316 includes an opening 344 through which light may pass. Also shown in FIGS. 3, 4 and 5 is an FNTD 352.

There are four blue LED openings 320, one blue LED opening 320 for each of four blue LEDs (not shown in FIGS. 3, 4 and 5) of camera head 302. There are also four NIR LED openings 324, one NIR LED opening 324 for each of four NIR LEDs (not shown in FIGS. 3, 4 and 5) of camera head 302.

Although the apparatus for obtaining green fluorescent contrast images of FNTDs and for obtaining near-infrared (NIR) diffuse reflection contrast images of FNTDs shown in FIGS. 3, 4 and 5 is designed to be part of a dosimeter reader, in some embodiments of the present invention, the apparatus for obtaining green fluorescent contrast images of FNTDs and for obtaining near-infrared (NIR) diffuse reflection contrast images of FNTDs may be a device separate from a dosimeter reader for FNTDs.

Figure 6:
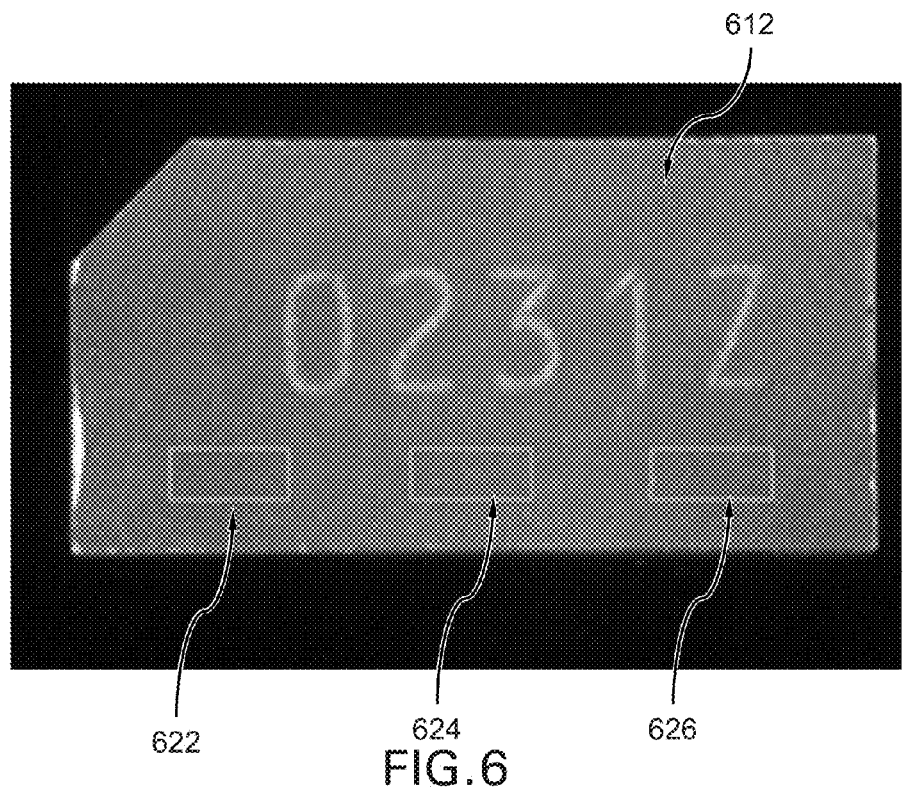
FIG. 6 is an image of an FNTD in green fluorescence contrast using the imaging camera head depicted FIG. 3.

FIG. 6 is a green fluorescence image of an FNTD 612 obtained by CMOS camera head in green fluorescence contrast (an emission band centered at 520 nm) under a blue LED light stimulation at 440+/−20 nm. This green fluorescence image is used for two purposes: (1) to read the ID engraved on the back side of the FNTD using image processing software and optical character recognition (OCR) and (2) to measure concentration of "green" color centers in three different areas (regions of interest (ROI)) 622, 624 and 626 of the detector corresponding to the position of three radiation converters used in an FNTD badge (Li-containing glass, polyethylene (PE), and polytetrafluoroethylene (PTFE). Average intensities of green fluorescence obtained for each of three converter areas are used as a measure of color center concentration to correct the results of FNTD dosimetric reading in analog processing mode.

Figure 7:
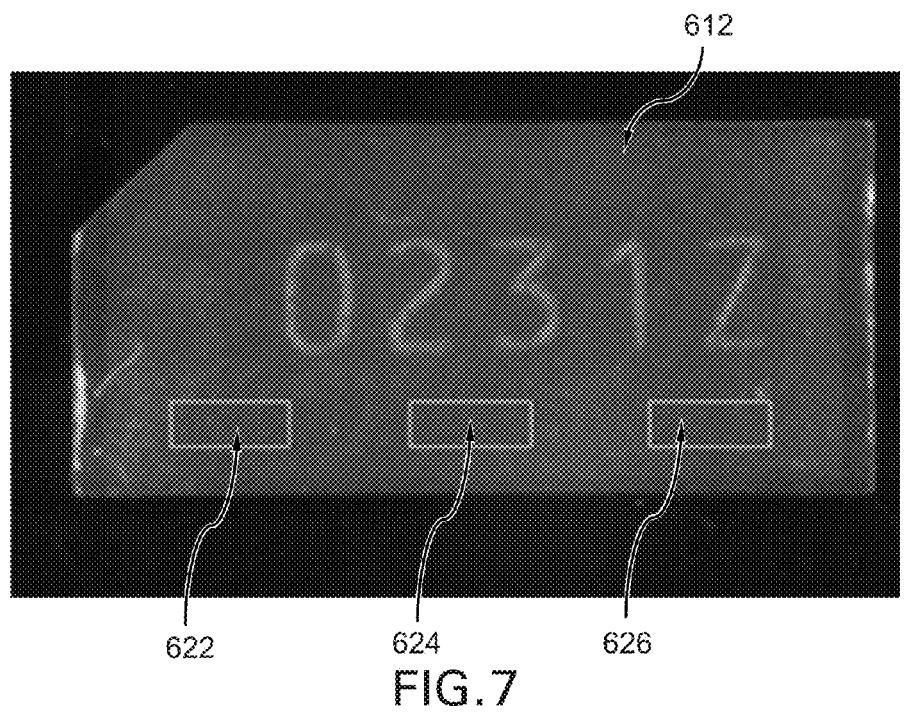
FIG. 7 is an image of the FNTD of FIG. 6 in near-infrared (NIR) diffuse reflection contrast using the imaging camera head depicted in FIG. 3.

FIG. 7 is the image of FNTD 612 acquired by the same CMOS camera head and is obtained in diffuse reflection mode under near-infrared (NIR) illumination at 900+/−50 nm. In contrast to the fluorescent imaging mode where the excitation and emission light are well separated by the wavelength, in diffuse reflection mode the image is obtained by the camera at the same wavelength as the illumination wavelength. This second, scatter image is needed to correct the measurement results from the green fluorescent imaging. The reason for this is that the intensity of a green fluorescence image depends on the scattering of both the blue excitation light and the green fluorescence itself by the back unpolished surface of the detector. Applying the correction based on the intensity of the scatter image improves correlation between the green fluorescence and measured absorbed dose.

Figure 8:
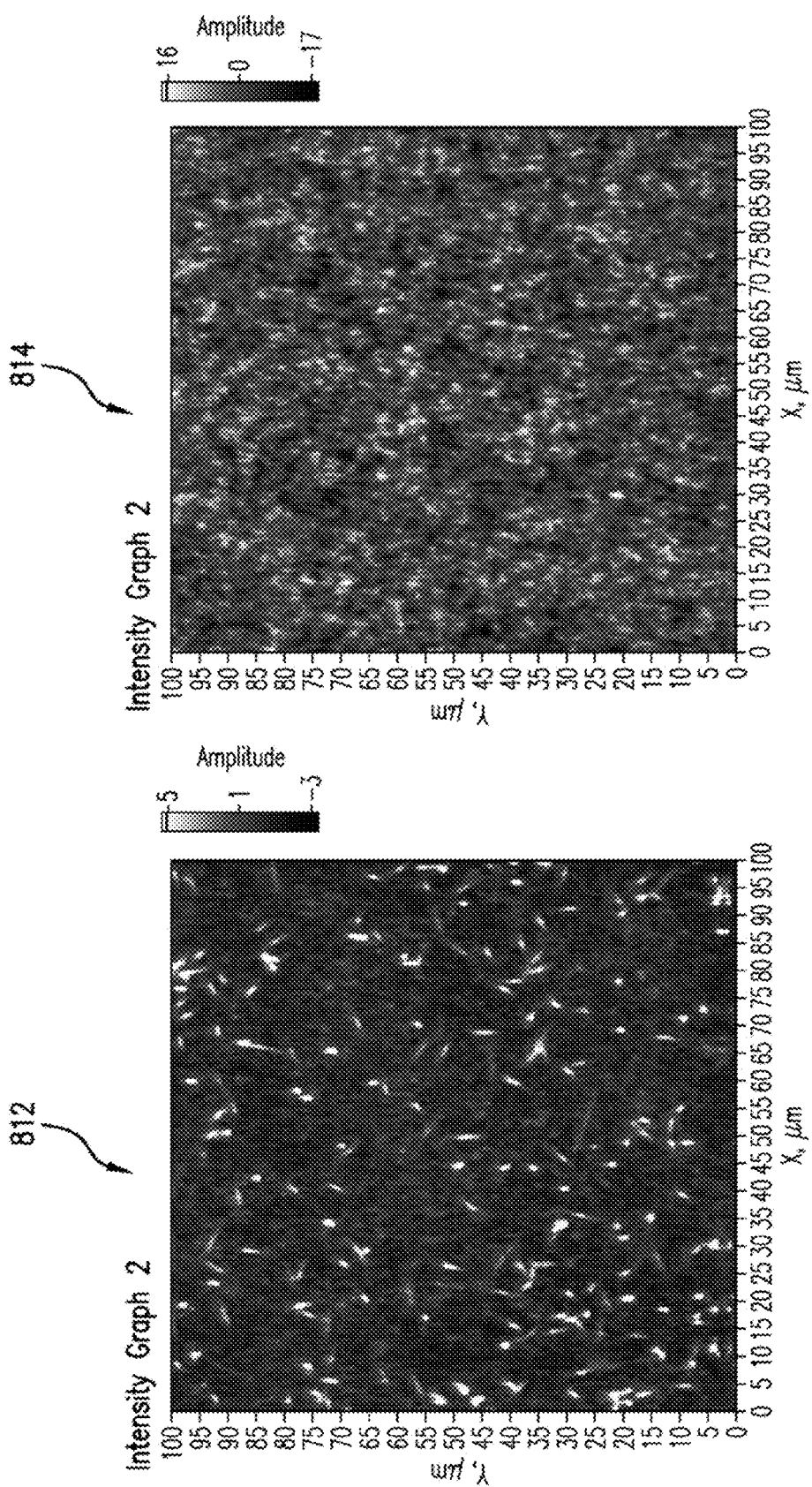
FIG. 8 shows fluorescent images of high dose irradiated detectors obtained with laser scanning fluorescent confocal optical head: left) 1 Sv of fast neutrons from bare AmBe source; right) 2 Sv of Cs-137 661 keV gamma photons.

FIG. 8 shows red fluorescent images 812 and 814 obtained with laser scanning fluorescent confocal optical head of the FNTD reader from FNTDs irradiated with high doses. Image 812 is an image for 1 Sv of fast neutrons from bare AmBe source; image 814 is for 2 Sv of Cs-137 661 keV gamma photons. These images illustrate high density of overlapping recoil proton tracks (in case of neutrons) and blobs of fluorescence caused by overlapping delta electrons (in case of high photon dose) that makes track counting difficult or impossible. For doses above approximately 50 mSv of total mixed neutron and photon dose analog processing mode of dose calculations is needed.

Figure 9:
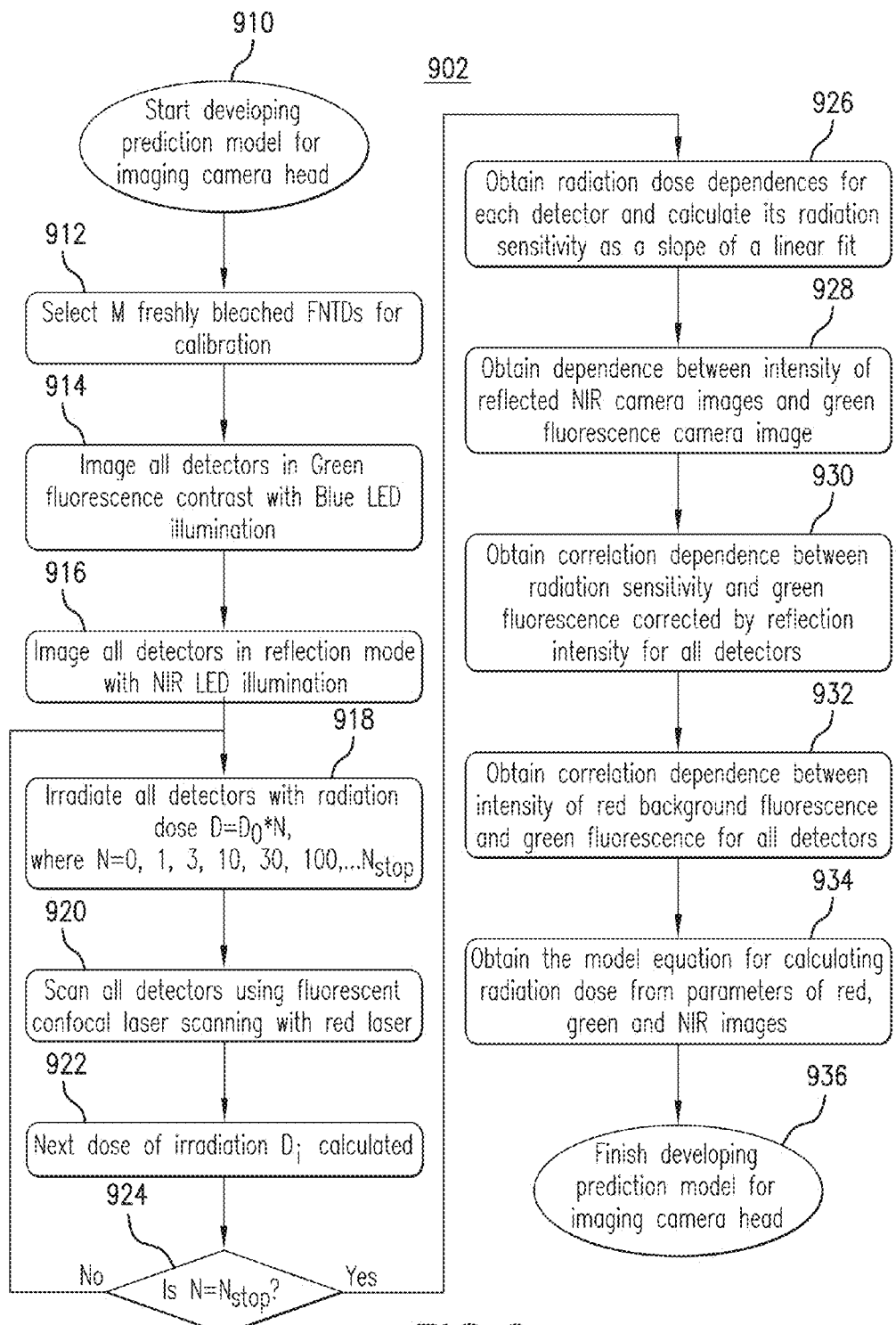
FIG. 9 is a flowchart showing a method for obtaining the prediction model and dose calculation equation from set of irradiated FNTDs and their images in red and green fluorescence contrast as well as in NIR diffuse reflection mode according to one embodiment of the present invention.

FIG. 9 is a flow chart of a method according to one embodiment of the present invention used for obtaining the prediction model and dose calculation equation from set of irradiated FNTDs and their images obtained in red and green fluorescence contrast as well as in NIR diffuse reflection contrast. FIG. 9 shows a flowchart of a calibration method 902 according to one embodiment of the present invention for obtaining all coefficients and parameters needed for establishing the relationship between green fluorescence and radiation induced red fluorescence for a FNTD reader using an imaging camera head, such as the imaging camera heads shown in FIGS. 2, 3, 4 and 5. At step 910 of method 902 is a start for developing a prediction model for an imaging camera head. At step 912, M freshly bleached FNTDs are selected for calibration. At step 914 all selected FNTDs are imaged in green fluorescence contrast with blue LED illumination, i.e., the FNTDs are exposed to blue excitation light to produce green emitted fluorescent light which is detected by a CMOS camera. At step 916, all of the FNTDs are imaged in diffuse reflection mode with NIR LED illumination, i.e., the FNTDs are exposed to NIR light and the diffused light reflected by the FNTDs is detected by the CMOS camera. At step 918, each respective FNTD is irradiated with a respective radiation dose of $D_j$, where $D_j=D_0 \times N_j$ for each FNTD and where the value of $N_j$ for each of the FNTDs are each different values. For example, for one set of FNTDs the values of $N_j$ may be $N_j=0$, 1, 3, 10, 30, 100, ... $N_{stop}$, where $N_{stop}$ is the highest $N_j$ value. At step 920, the FNTDs are scanned using fluorescent confocal laser scanning imaging with a red laser and analog parameters average fluorescent intensity or PSI are obtained for each detector. After that at step 922, the next dose of irradiation $D_i$ is calculated by incrementing index j (j=j+1) and obtaining the next dose for irradiating all FNTDs. At step 924, it is determined if the maximum dose has been reached, i.e., steps 918 and 920 have been performed on the FNTD having the maximum radiation dose. If the maximum dose has not been reached, steps 918 920, and 922 are repeated until the maximum dose is reached. For example, for a set of FNTDs where the highest value of $N_j$ is $N_{stop}$, the maximum dose is reached when $D_j=D_0 \times N_{stop}$.

Figure 11:
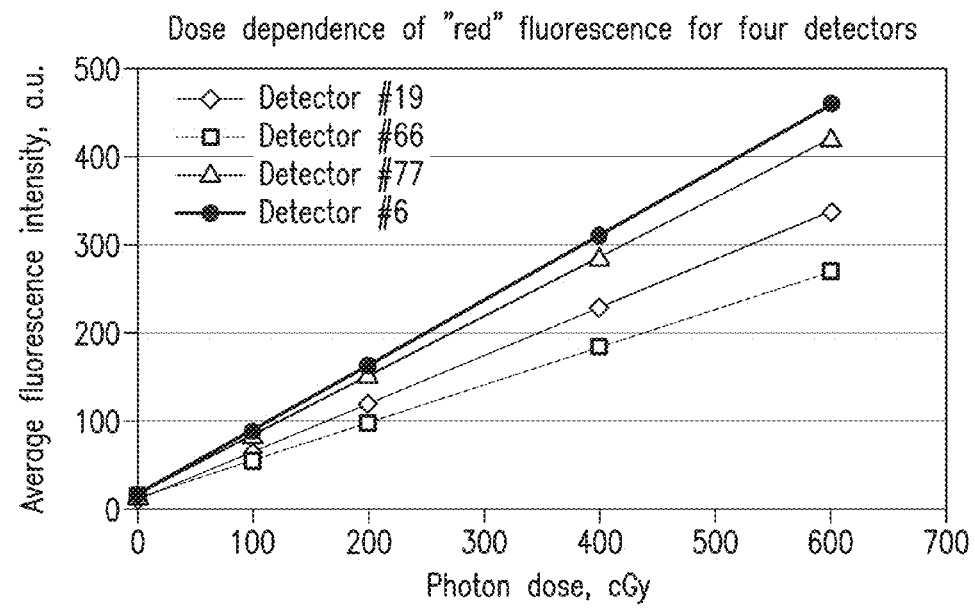
FIG. 11 is a graph showing dose dependence of radiation-induced red fluorescence (average intensity for ROI) for several FNTDs irradiated with X-rays photons.
Figure 12:
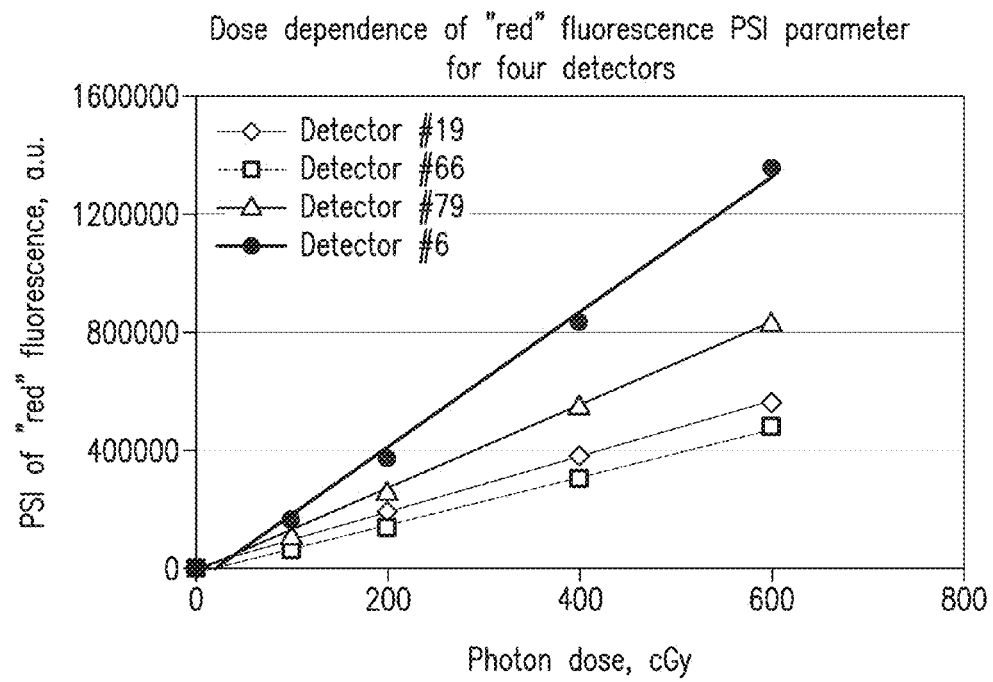
FIG. 12 is a graph showing dose dependence of radiation-induced red fluorescence (Power Spectral Integral) for several FNTDs irradiated with X-rays photons.

After steps 918, 920 and 922 have been conducted on all of the FNTDs (i=0, 1, 2, . . . , M), at step 926, the radiation dose dependence for each FNTD is determined and the radiation sensitivity $S_{red,i}$ for each of the FNTDs is calculated as a slope of a linear fit of red fluorescent intensity as a function of dose (see example shown in FIGS. 11 and 12). In a simple way with a single dose measurement the sensitivity of red fluorescence is determined based on equation (1) below:

$$S_{red,i}=(F_{red,i}-B_{red,i})/D_{deliv} \quad (1)$$

where $F_{red,i}$ is red fluorescence intensity, $B_{red,i}$ is a background fluorescence signal obtained from unirradiated detector (j=0) and $D_{deliv}$ is the radiation dose delivered to the FNTD.

At step 928 the correlation dependence $F_{green}^s$ between the intensity of green fluorescence camera images $F_{green}$ and the intensity of diffused reflection NIR camera images $F_{diff}$ is determined. The correlation is a linear fit function shown in equation (2) below:

$$F_{green}^s=a_1 F_{green}/F_{diff}-b_1 \quad (2)$$

Coefficient $a_1$ in equation (2) may be determined plotting $F_{green}^s$ vs. $F_{green}/F_{diff}$ and determining the slope of the best linear fit. Coefficient $b_1$ in equation (2) may be determined by where the best linear fit crosses the y axis. For a particular FNTD reader, equation (2) may be referred to as the correlation dependence between green fluorescence camera image intensity and near-infrared (NIR) camera image intensity for the FNTD reader.

At step 930 the correlation dependence between radiation sensitivity coefficients $S_{red}$ and green fluorescence corrected by NIR diffuse reflection image intensity $F_{green}^s$ for all detectors (see example in FIG. 12) is determined. The correlation is a linear fit function shown in equation (3) below:

$$S_{red}=a_2 F_{green}^s-b_2 \quad (3)$$

Coefficient $a_2$ in equation (3) may be determined plotting $S_{red}$ vs. $F_{green}^s$ and determining the slope of the best linear fit. Coefficient $b_2$ in equation (3) may be determined by where the best linear fit crosses the y axis. For a particular FNTD reader, equation (3) may be referred to as the correlation dependence between radiation sensitivity coefficients intensity and green fluorescence corrected by NIR diffuse reflection image intensity for the FNTD reader.

Figure 14:
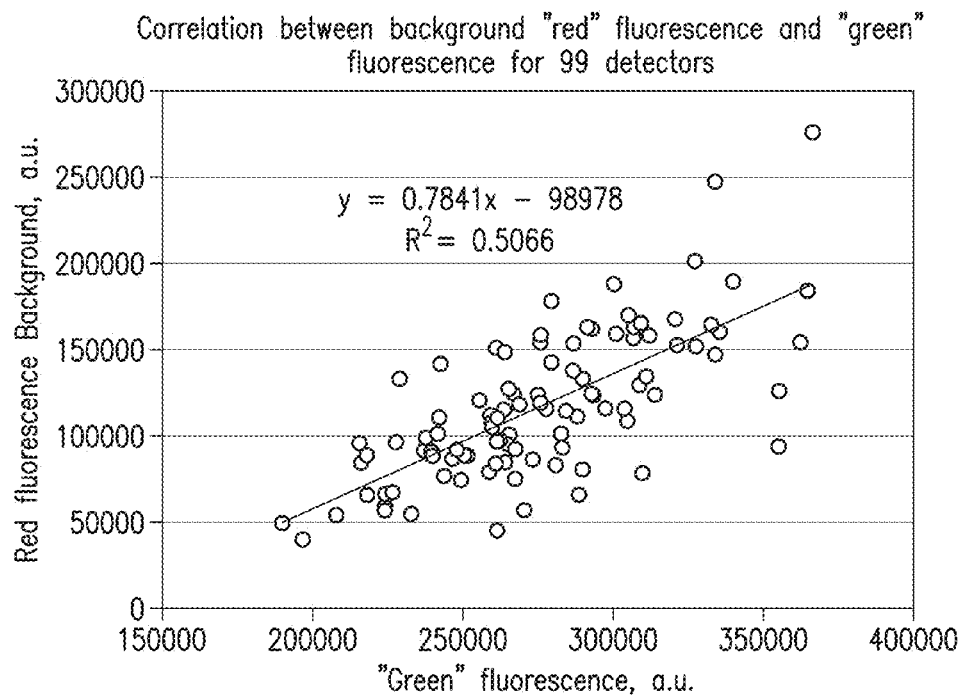
FIG. 14 is a plot showing the correlation dependence between "green" fluorescence intensity and background of "red fluorescence" for 99 detectors irradiated with X-ray photons.

At step 932 the correlation dependence between intensity of red background fluorescence $B_{red}$ and intensity of green fluorescence is determined for freshly bleached detectors (see example in FIG. 14). The correlation is a linear fit function shown in equation (4) below:

$$B_{red}=a_3 F_{green}^s-b_3 \quad (4)$$

Coefficient $a_3$ in equation (4) may be determined plotting $B_{red}$ vs. $F_{green}^s$ and determining the slope of the best linear fit. Coefficient $b_3$ in equation (4) may be determined by where the best linear fit crosses the y axis. For a particular FNTD reader, equation (4) may be referred to as the correlation dependence between intensity of red background fluorescence and intensity of green fluorescence for the FNTD reader.

At step 934, a model equation is determined for calculating radiation dose from parameters of "red fluorescence", "green fluorescence" and NIR diffuse reflection images. This equation is based on equations (2), (3) and (4) and is shown below as equation (5):

$$D=(F_{red}-B_{red})/S_{red} \quad (5)$$

At step 936 indicates the finish of developing the prediction model.

Calibration method 902 is a calibration procedure for an analog mode of dose measurements. Calibration method need only be performed once during instrument calibration but can be repeated periodically as a quality assurance procedure. The correction functions (2), (3) and (4) of steps 928, 930 and 932, respectively, and the corresponding coefficients of these functions are stored in the instrument configuration file. Also, although for purposes of illustration, the determination of coefficients $a_1$, $a_2$, $a_3$, $b_1$, $b_2$, $b_3$ are described above as if physical lines are plotted to determine these coefficients, the coefficients may be determined purely mathematically by a computer without ever displaying the plots for the various lines. A computer used to determine the coefficients for calibration may be part of a dosimeter reader or may be part of a separate apparatus.

Figure 10:
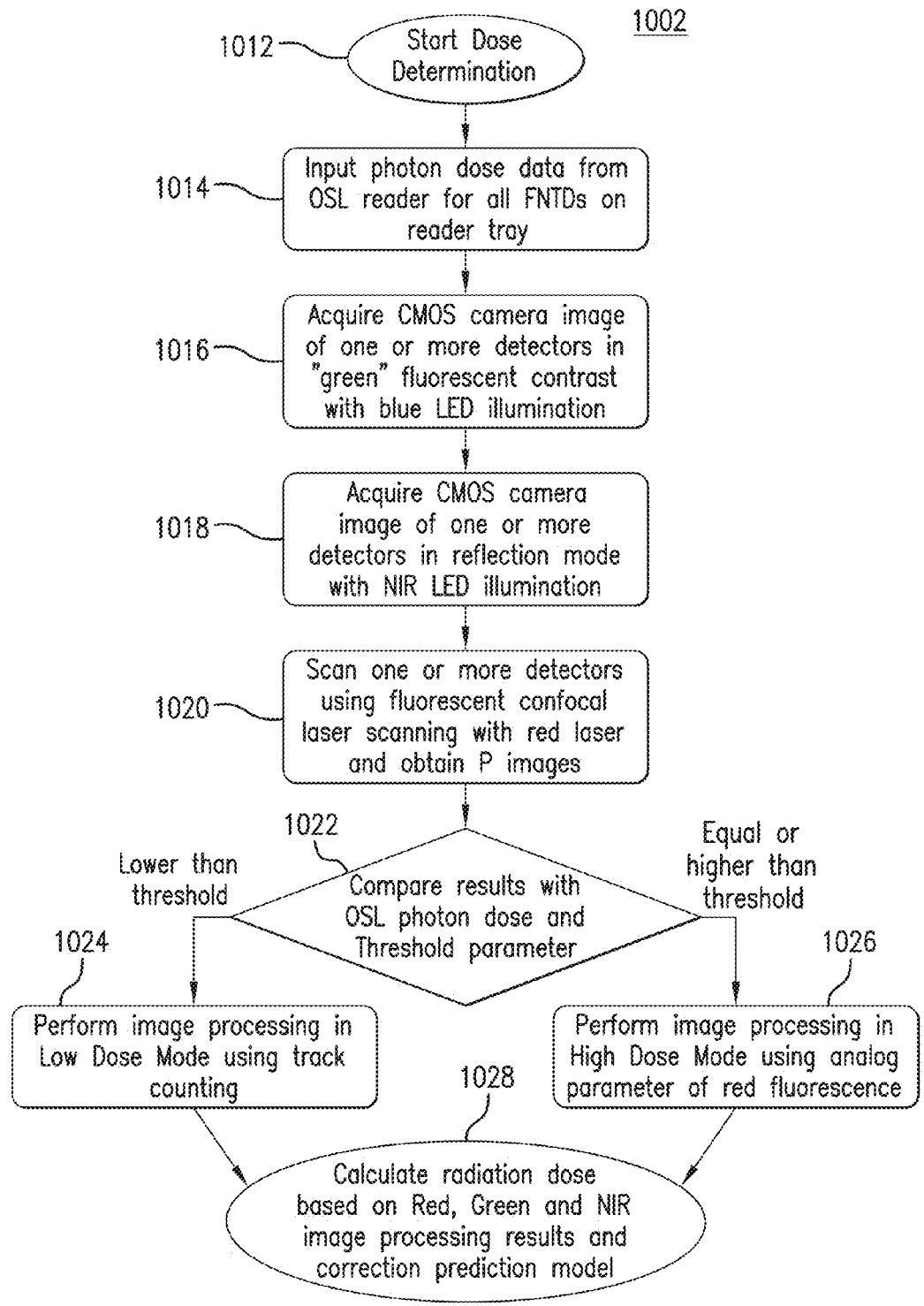
FIG. 10 is a flowchart showing a method for determining radiation dose from a set of images in red and green fluorescence contrast as well as in NIR diffuse reflection mode according to one embodiment of the present invention.

FIG. 10 shows a flow chart of a method 1002 for determining unknown radiation dose from a detector by processing set of images in red and green fluorescence contrast as well as in NIR diffuse reflection contrast. Method 1002 is a procedure for measuring and calculating the dose for FNTD irradiated with unknown dose taking as input data results of green fluorescence, NIR diffuse reflection intensity, and "red fluorescence" measurements. At step 1012 method 1002 is started. At step 1014 photon dose data from an optically stimulated luminescence (OSL) reader is input into a computer for all FNTDs loaded on a reader tray. At step 1016, an image in green fluorescence contrast under blue LED illumination is acquired by the CMOS camera head for one or more FNTDs. At step 1018 an image in NIR diffuse reflection contrast with NIR illumination is acquired by the CMOS camera head for one or more of the FNTDs. At step 1020 one or more of the FNTDs are scanned with red laser using fluorescent confocal laser scanning optics of the FNTD reader to obtain P number of images. At step 1022 the OSL photon dose obtained from the same badge that contained the FNTD is compared with a preset threshold parameter $D_{thr}$. If the OSL photon dose is determined to be less than $D_{thr}$, then at step 1024 the dose calculations for the FNTDs are performed in Low Dose mode using a track counting method. If the OSL photon dose is equal to or greater than $D_{thr}$, then at step 1026 the calculations are performed in a High Dose mode at step 1028 using analog values of red ($F_{red}$) and green fluorescence ($F_{green}$) and NIR diffuse reflection ($F_{diff}$) according to equation (5). The parameters $B_{red}$, $S_{red}$ in equation (5) are calculated from the correction functions of equations (2), (3) and (4) with parameters obtained during calibration procedure described above and the values of $F_{green}$, $F_{diff}$ and $F_{red}$ are measured for each FNTD detector. Steps 1014, 1016, 1018, 1020, 1022, 1024, 1026 and 1028 of method 1002 may be performed for each of one or more converter areas for further dose correction in mixed neutron-photon fields.

In at least some embodiments of the present invention, it is desirable that above described calibration procedure be performed and parameters listed above be obtained for different types and energies of radiations (photons, neutrons, electrons, heavy ions, etc.)

FIG. 11 illustrates dose dependences of radiation-induced red fluorescence (average intensity for ROI) for several FNTDs irradiated with X-rays photons.

FIG. 12 illustrates dose dependences of radiation-induced red fluorescence (Power Spectral Integral) for several FNTDs irradiated with X-rays photons.

Based on data similar to FIGS. 11 and 12, and obtained for all 99 FNTDs selected for calibration, the slopes of dose dependences needed to calculated, the sensitivity coefficients $S_{red}$ and background values $B_{red}$ are obtained by linear fit of each 99 dose dependences. Those data are used to obtain and process the correlation dependences on FIGS. 13 and 14.

Figure 13:
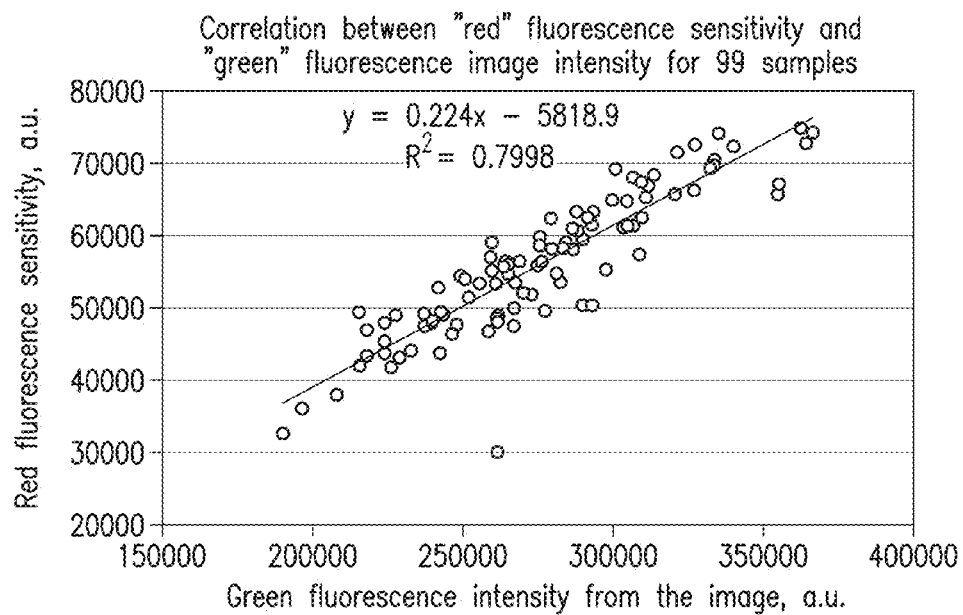
FIG. 13 is a plot showing the correlation dependence between "green" fluorescence intensity and sensitivity coefficient of radiation-induced "red fluorescence" for 99 detectors irradiated with X-ray photons.

FIG. 13 shows the scatter plot and the correlation dependence between "green" fluorescence intensities $F_{green}$ and sensitivity coefficient $S_{red}$ (slopes of dose dependences in FIG. 11) of radiation-induced "red fluorescence" for 99 detectors irradiated with X-ray photons. This correlation dependence and coefficients of linear regression are used to correct the dose readings obtained using red confocal fluorescent imaging. In FIG. 13 $a_2=0.224$ and $b_2=5818.9$ are obtained by linear fit of the data.

FIG. 14 is a plot showing the correlation dependence between "green" fluorescence intensity $F_{green}$ and background of "red fluorescence" (free parameter $b_1$ of dose dependence linear fit) for 99 unirradiated detectors. This plot is used in developing of prediction model to calculate the expected red fluorescence background signal of unirradiated detector. The value of this predicted background is used for subtraction from the red fluorescence signal of detector irradiated with unknown dose. In FIG. 14 $a_3=0.7841$ and $b_3=98978$ are obtained by linear fit of the data.

Figure 15:
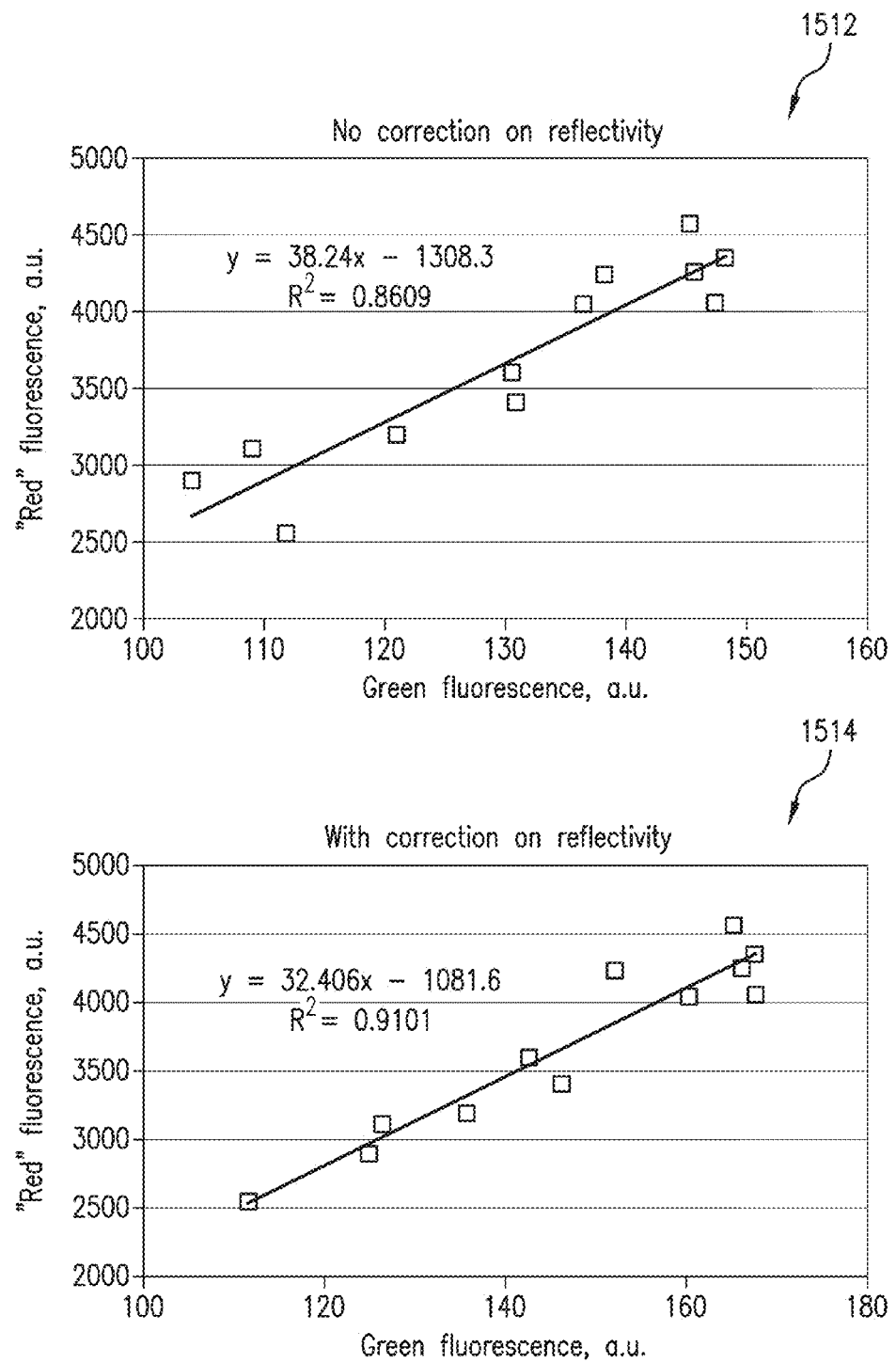
FIG. 15 shows two plots illustrating the effect of both NIR diffuse reflection correction and "green" fluorescence correction on uncertainty of FNTD dosimetric measurements in analog mode using "red fluorescence."

FIG. 15 illustrates the effect of both NIR diffuse reflection correction and "green" fluorescence correction on uncertainty of FNTD dosimetric measurements in analog mode using "red fluorescence." Plot 1512 shows dosimetric measurements with no correction on reflectivity. Plot 1514 shows dosimetric measurements with a correction on reflectivity. As a result of correction on the detector NIR reflectivity the correlation coefficient $R^2$ between green and red fluorescence signals is increased from 0.861 to 0.910.

Figure 16:
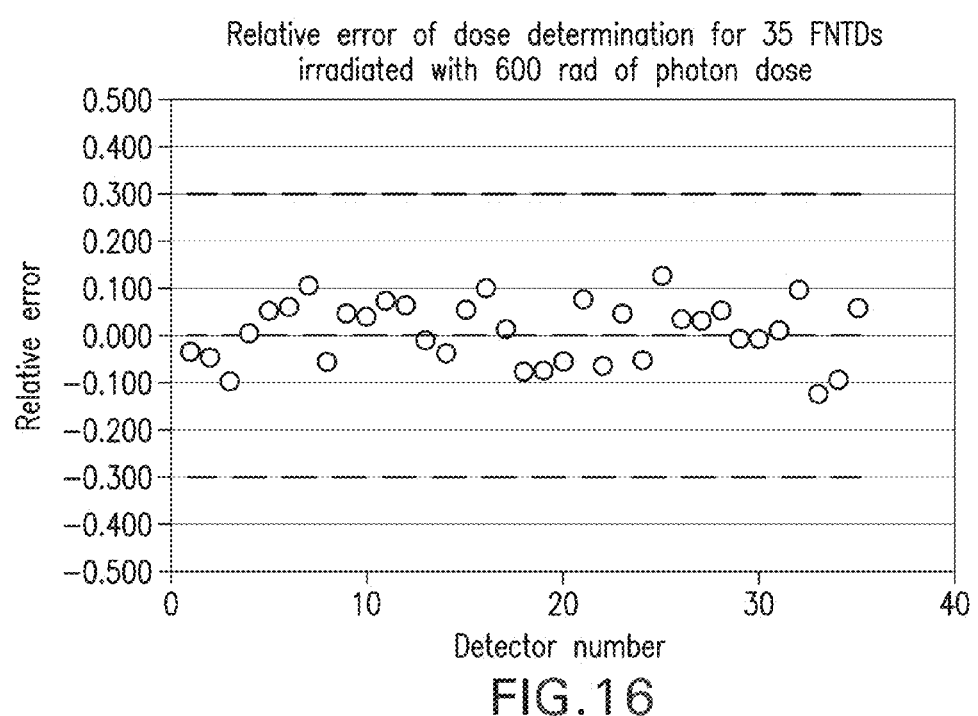
FIG. 16 is a plot of relative error of dose determination using described correction technique for 35 randomly selected detectors irradiated with 600 cGy of photon dose.

FIG. 16 show relative error of dose determination using the method of the present invention technique for 35 randomly selected FNTDs irradiated with 600 cGy of photon dose. Dash lines at +0.3 and −0.3 indicate maximum allowed error limits.

Figure 17:
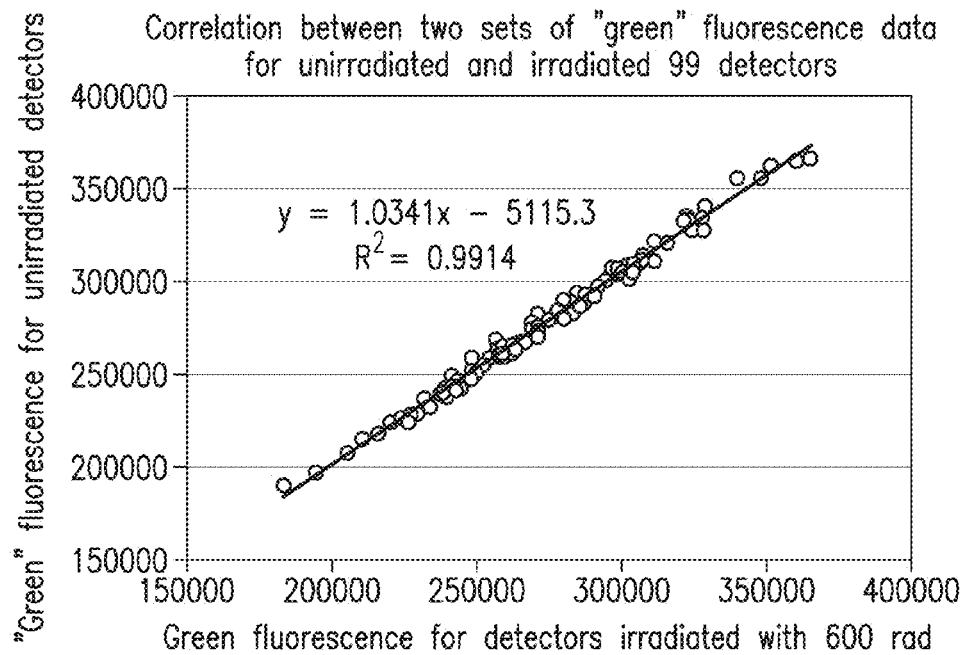
FIG. 17 is a plot showing the correlation between two sets of "green" fluorescence data for 99 unirradiated and irradiated detectors, illustrating that "green" fluorescence is not significantly affected by irradiation with doses below 1000 rad.

FIG. 17 is a correlation between two sets of "green" fluorescence data for 99 unirradiated and irradiated detectors illustrating that "green" fluorescence is not significantly affected by irradiation below 1000 rad.

Figure 18:
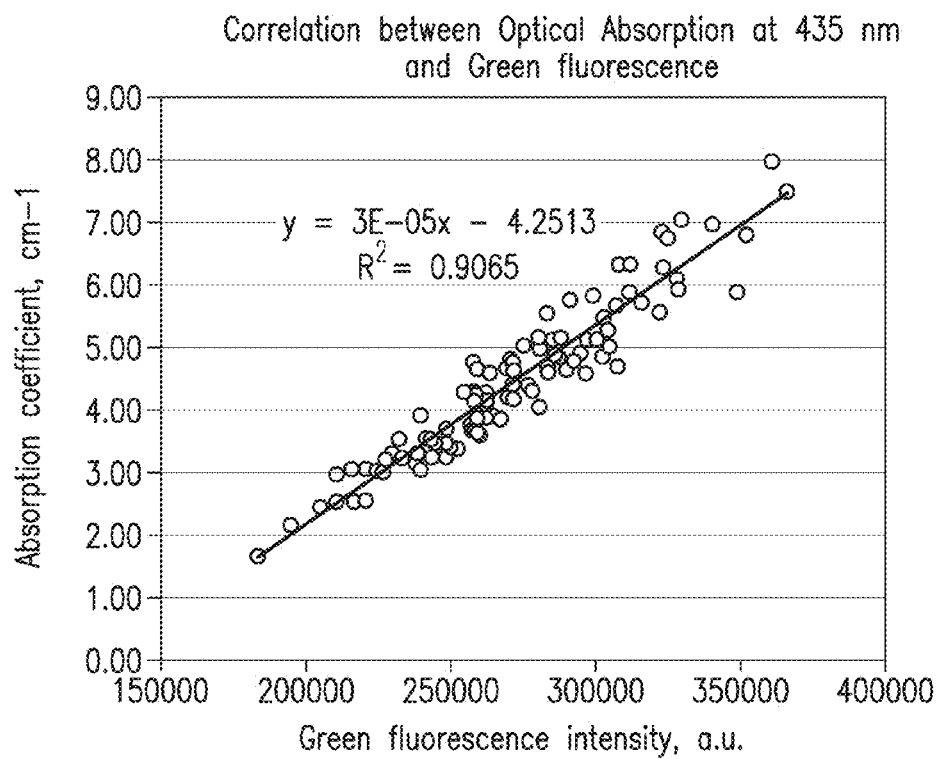
FIG. 18 is a plot showing the correlation between color center concentration determined by optical absorption and by "green" fluorescence.

FIG. 18 is a correlation between color center concentration determined by optical absorption and by "green" fluorescence and confirms that green fluorescence intensity is a good measure of color center concentration in $Al_2O_3$:C,Mg crystals.

In one embodiment of the present invention, suitable red lasers for use in the method described above have a wavelength between 610 and 660 nm. In one embodiment of the present invention, Suitable red lasers for use in the method described above include 635 to 640 nm single mode diode laser, or a 633 nm He—Ne gas laser, or any other single mode laser with the wavelength between 600 to 640 nm.

In one embodiment of the present invention employing NIR illumination and NIR diffuse reflection contrast, the NIR diffuse illumination light and the NIR reflected light each have a wavelength between 800 and 1000 nm.

In one embodiment of the present invention employing "red fluorescent" contrast, the "red fluorescent" light has a wavelength between 680 and 850 nm.

In one embodiment of the present invention used on an FNTD comprising an aluminum oxide luminescent material, a blue excitation light may be used having a wavelength between 410 and 470 nm. Such a blue excitation light may be used to stimulate the luminescent material to a green fluorescent light having a wavelength between 470 and 570 nm that may be used to generate green fluorescent contrast images.

Although in the description above and in the examples below, green fluorescent light is used to produce calibrated radiation dose measurements, various colors of fluorescent light such a blue, yellow, orange and red, etc. may be used to produce calibrated radiation dose measurements in embodiments of the present invention depending on the properties of the luminescent material whose exposure to radiation is being measured.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Dual-Color Fluorescent/Near-Infrared (NIR) Imaging and Sensitivity Calibration

An imaging optical head that provides coloration-correction is added to an existing FNTD reader design such as described in M. S. Akselrod, V. V. Fomenko, J. A. Bartz, and T. L. Haslett, "Commercial neutron dosimetry system based on fluorescent nuclear track detector technology, *Rad. Prot. Dosim.* (2013) (Reference 2). In one embodiment of the present invention, two sets of light-emitting diodes (LEDs) may be employed: the blue LEDs emitting at 447 nm and near-infrared (NIR) LEDs emitting at 940 nm. The LEDs are arranged to illuminate the FNTD at an oblique angle so that the fluorescence and the IR images are collected non-specularly. A relay optical pair images the FNTD on the CMOS camera sensor with a demagnification of two. The long-pass optical filter with 50% transmission at 515 nm, installed in front of the camera sensor, separates the excitation blue light from the green fluorescence. At the same time, this filter allows the transmission of the NIR LED light scattered by the detector surfaces during the acquisition of the detector image in diffuse-reflection contrast. To calibrate the radiation sensitivity of each detector, two CMOS images are obtained for each FNTD before starting dosimetric measurements using confocal laser scanning fluorescence imaging. First, the detector image is obtained in green fluorescence contrast under the blue LED excitation. Then, the blue LEDs are turned off and NIR LED illumination is used to obtain the second image of the detector to measure the amount of diffuse reflection that the lapped detector surface introduces. Both, the green fluorescent image and the NIR diffuse reflection image can be used to perform optical character recognition to read the alpha-numerical ID engraved on the back side of the detector. The dual-color imaging and the ID readout procedure are performed for all detectors loaded on the FNTD reader tray. The average intensities of the green fluorescence and IR diffuse reflection are determined only for specific region of interest (ROI) of the detector corresponding to the area of dosimetric imaging with confocal laser scanning.

Since the procedure for dose calculation involves correcting the sensitivity of FNTDs in three converter locations by the intensity of green-fluorescence and that of IR diffuse reflection, it is important to ensure the uniformity of detector illumination with the LEDs and uniformity of the CMOS camera sensor field of view (FOV). The flatness of the FOV is ensured through careful optical design that utilized four blue and four IR LEDs. Remaining variations in the illumination were corrected by calibration and software correction.

Example 2

Relationship Between PSI Parameter and Color Center Concentration

To calibrate the radiation sensitivity of FNTDs as a function of color center concentration, a set of FNTDs was first optically bleached to erase any accumulated dose and then, irradiated to a series of X-ray doses from 3 to 3,000 cGy. Prior to dosimetric, confocal laser scanning fluorescence readout, each of the FNTDs was imaged by the CMOS optical head, described above, in both green fluorescence and IR contrasts by sequential illumination of each detector with blue and NIR LEDs. Then, the average intensities of green fluorescence $F_{green}$ and NIR diffuse reflection images, $F_{diff}$, were calculated in the ROIs corresponding to the confocal scan areas. The influence of the diffuse reflection at the detector surfaces was taken into account by calculating a corrected value of green fluorescence using equation (2).

At each dose, the FNTDs were read out to obtain images of confocal "red fluorescence" caused by the radiation-induced $F_2^{2+}$ (2Mg) centers. Finally confocal fluorescent images were processed to obtain the average PSI values for each FNTD.

A strong correlation between the average PSI and the crystal coloration, expressed as the magnitude of the green fluorescence, is evident. Although the correlation coefficients were relatively low ($R^2=0.48$) when the uncorrected green fluorescence was used, correcting for the detector back surface diffuse reflection significantly improves the correlation coefficient to 0.79 thereby reducing the dose estimation error. Thus, it was demonstrated that the intensity of green fluorescence produced by $F_2^{2+}$ (2Mg) centers corrected by the amount of diffuse reflection (scatter) from the lapped surface of the detector can be used for radiation sensitivity calibration of each FNTD nondestructively, without the need for post-readout calibration using test irradiations. During reader calibration the radiation sensitivity $S_{red,i}$ for each detector was determined by the slope of the dose dependence of the analog parameter. Then, the correlation between the radiation sensitivities $S_{red,i}$ for all detectors and their corrected green fluorescence intensity, $F_{green,i}^{S}$, was established (FIG. 13).

For accurate measurement of low doses, the value estimation of the PSI analog parameter at zero dose, i.e. the background PSI value $B_i$, is additionally required for each detector. The background PSI parameter can be predicted, although less precisely than the sensitivity, from the color center concentration measurements using green fluorescence and NIR diffuse reflection imaging as demonstrated by the correlation dependences as shown in FIG. 14. Thus, the measurement of the green fluorescence on an individual FNTD allows one to evaluate two parameters required for dose calculation: the sensitivity of the FNTD $S_i$ and the background PSI value $B_i$.

Example 3

Effect of Irradiation on Color-Center Concentration and Green Fluorescence

Since irradiation of the FNTD material involves a radiochromic transformation between the $F_2^{2+}$ (2Mg) and $F_2^+$ (2Mg) color centers bands (Reference 1), it is necessary to investigate the stability of the $F_2^{2+}$ (2Mg) band intensity over a wide range of doses. For the proposed coloration correction algorithm to be practical, the intensity of the $F_2^{2+}$ (2Mg) optical absorption and fluorescence band should not change significantly with dose. Experiments have been conducted to investigate the dose dependence of the $F_2^{2+}$ (2Mg) band. 110 FNTDs were irradiated with various doses of X-rays (40 kV), Cs-137 gamma and AmBe neutrons. It has been found, that for the investigated radiation fields, in the dose range of up to 3000 cGy, the intensity of green fluorescence of the $F_2^{2+}$ (2Mg) centers does not change to an observable amount. The correlation coefficient of 0.991 and slope of 1.03 between the intensities of the $F_2^{2+}$ (2Mg) scatter-corrected green fluorescence measured before and after the irradiation for 110 of FNTDs of various coloration irradiated with 30 Gy of X-rays (40 kV) as shown in FIG. 17 proves this claim. The green fluorescence remained unchanged after X-ray irradiation since the green fluorescence of the X-ray irradiated FNTDs is related to that of unirradiated crystals linearly with a slope of 1. The same trend holds for fields of $^{137}$Cs photons, AmBe neutrons and mixed gamma-neutrons fields.

A calibration is performed before applying the developed sensitivity-correction algorithm to the calculation of unknown dose. 99 detectors were selected and their images were obtained in green-fluorescence and NIR diffuse reflection contrast as described above. The parameter $F^S_{green}$, a ratio of green-fluorescence to IR diffuse-reflection intensities, was calculated for each detector. Then, multiple (up to 100) confocal "red fluorescence" images were obtained and analog PSI parameter was calculated for unirradiated bleached detectors and the same detectors sequentially irradiated with X-ray photons with doses ranging from 3 to 3000 cGy. The PSI analog parameter was obtained for each detector at each dose. The dose dependence of PSI for each detector was used to obtain the background zero-dose values $B_{red,i}$, and radiation sensitivity, i.e. the slope $S_{red,i}$.

Further, correlations between the radiation sensitivity ($S_{red,i}$) and the diffuse reflection corrected green fluorescence intensity ($F_{green}^{S}$) were processed, plotted and the coefficients of the linear fit equation (3), $a_2$ and $b_2$, were obtained.

Similar correlation dependence was obtained between the intensity of background "red fluorescence" (PSI parameter) and green fluorescence measured on freshly bleached detectors and the coefficients of linear regression equation (4) $a_3$ and $b_3$ were calculated.

In this study, the parameters $a_2$, $b_2$, $a_3$, and $b_3$ of equations (3) and (4) were determined for the X-ray radiation field and were successfully applied for $^{137}Cs$ and fast-neutron fields as described in Examples 4 and 5 below.

In regular FNTD dosimetry system operation, the unknown dose of radiation from an uncalibrated FNTD detector can be determined by first imaging the detector with CMOS optical head in green fluorescent and NIR diffuse reflection contrast to obtain values of $F_{green}$ and $F_{diff}$ and then scanning all three converter areas in confocal fluorescence geometry to obtain radiation-induced "red fluorescent" images and PSI dosimetric parameters $F_{red, k}$ where (k=1, 2, and 3 represent three converter areas). The dose is then calculated as shown in equation (5) previously presented above.

Example 4

Testing the Algorithm

To test the developed procedure, 110 detectors were irradiated with 40 kVp X-rays in the dose range from 3 to 3000 cGy. The doses were obtained using the algorithm described above. The nonlinearity of dose response above 100 cGy is obvious and requires further correction with a $3^{rd}$-order polynomial. The application of nonlinear correction significantly improves the dose dependences.

Example 5

Performance of FNTDs in High Dose, Mixed, Neutron Photon Fields

Further tests were performed with mixtures of fast neutrons produced by a burst reactor and $^{137}Cs$ gamma photons with ratios 1:3, 1:1 and 3:1.

Separation of neutron and gamma doses in mixed fields can be conducted in analog mode as described previously (References 1, 2, 3 and 4). In these tests, FNTDs were mounted in polyethylene (PE) holders, designed to cover the central part of the FNTD crystal with PE and the other half with polytetrafluoroethylene (PTFE). Confocal "red fluorescence" images, obtained from the Teflon-covered detector part, provided a measure of the photon dose, whereas images obtained from the detector part covered by the PE converter provided dose information about both neutrons and photons. The confocal "red fluorescence" images, green fluorescence and NIR diffuse reflection images were acquired from the same FNTD crystal within ROI behind both PE and PTFE converters. These three types of images were then processed to calculate the PSI values and corresponding doses for PE and PTFE converter areas. By subtracting the dose determined from the PTFE part of the detector from that determined from the PE part, neutron contribution to the total dose was determined. The neutron doses can be determined essentially within a ±30% error margin for mixed neutron-gamma fields when γ/n dose ratio is less than 3. This example demonstrates the applicability of the sensitivity calibration method for mixed neutron-gamma fields.

REFERENCES

The following references are referred to above and are incorporated herein by reference:

1. Akselrod M. S. and Sykora G. J., "Fluorescent Nuclear Track Detector technology—a new way to do passive solid state dosimetry," *Radiat. Meas.*, 46 1671-1679 (2011).
2. Akselrod, M. S., Fomenko, V. V., Bartz, J. A., Haslett, T. L., "Commercial neutron dosimetry system based on fluorescent nuclear track detector technology," *Rad. Prot. Dosim.* (2013).
3. Sykora, G. J. and Akselrod, M. S., "Spatial frequency analysis of fluorescent nuclear track detectors irradiated in mixed neutron-photon fields," *Radiat. Meas.*, 45, (10) 1197-1200, (2010)
4. Sykora, G. J. and Akselrod, M. S., "*Novel fluorescent nuclear track detector technology for mixed neutron-gamma fields, Radiation Measurements.,*" *Radiat. Meas.* 45 (3-6), 594-598 (2010).
5. Sykora, G. J. and Akselrod, M. S., "Photoluminescence study of photochromically and radiochromically transformed $Al_2O_3$:C,Mg crystals used for fluorescent nuclear track detectors," *Radiat. Meas.* 45 (3-6) 631-634 (2010).
6. Sykora, G. J., Akselrod, M. S., Vanhavere, F., Performance of Fluorescence Nuclear Track Detectors in Monoenergetic and Broad Spectrum Neutron Fields. Radiat. Meas. 44, 988-991 (2009).
7. Sykora, G. J., Salasky, M., and Akselrod, M. S., "Properties of novel fluorescent nuclear track detectors for use in passive neutron dosimetry," *Radiat. Meas.* 43, 1017-1023 (2008),
8. Benton, E. V. Oswald, R. A. Frank, A. L. Wheeler, R. V., "Proton-recoil neutron dosimeter for personnel monitoring," *Health Phys.* 40, 801-809 (1981).
9. Benton, E. V., Ogura, K., Frank, A. L., Atallah, T. M. and Rowe, V., "Response of different types of CR-39 to energetic ions," *Nuclear Tracks* 12, 79-82 (1986).
10. Bartz, J. A. Sykora, G. J. Bräuer-Krisch, and E. Akselrod, M. S., "Imaging and dosimetry of synchrotron microbeam with aluminum oxide fluorescent detectors," *Radiat. Meas.*, 46 1936-1939 (2011).
11. Sykora, J., Akselrod, M. S., Benton, E. R. and Yasuda, N., "Spectroscopic properties of novel fluorescent nuclear track detectors for high and low LET charged particles.," *Radiat. Meas.* 43, 422-426 (2008).
12. Bartz, J. A., Zeissler, C. J., Fomenko, V. V., Akselrod, M. S., "An imaging spectrometer based on high resolution microscopy of fluorescent aluminum oxide crystal detectors," *Radiat. Meas.*, In Press, Corrected Proof, Available online 27 Feb. 2013.
13. Niklas, M., Melzig, C., Abdollahi, A., Bartz, J., Akselrod, M. S., Debus, J., Jäkel, O. and Greilich, S. "Spatial correlation between traversal and cellular response in ion radiotherapy—Towards single track spectroscopy," *Radiat. Meas.*, In Press, Corrected Proof, Available online 21 Feb. 2013
14. ANSI N13.11-2009 American National Standard for Dosimetry—*Personnel Dosimetry Performance—Criteria for Testing* (2009).
15. ISO-21909-1, Passive neutron dosimetry systems—Part 1: Performance and test requirements for personal dosimetry. April 2013 (draft).

All documents, patents, journal articles and other materials cited in the present application are incorporated herein by reference.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising the following steps:
   (a) adjusting a radiation dose measurement for a fluorescent nuclear track detector based on a plurality of fluorescence contrast images for the fluorescent nuclear track detector to thereby produce a calibrated radiation dose measurement, and
   (b) displaying the calibrated radiation dose measurement to a user and/or saving the calibrated radiation dose measurement to a storage medium,
   wherein the fluorescent nuclear track detector comprises a luminescent material,
   wherein the radiation dose measurement is based on one or more fluorescent light measurements produced by fluorescent imaging of the fluorescent nuclear track detector using excitation light from a laser having a first wavelength, and
   wherein the plurality of fluorescence contrast images are produced by illuminating the fluorescent nuclear track detector with excitation light having a second wavelength.

2. The method of claim 1, wherein the radiation dose measurement is based on one or more fluorescent light measurements produced by confocal laser scanning fluorescent imaging of the fluorescent nuclear track detector.

3. The method of claim 1, wherein the one or more fluorescent light measurements are utilized to determine a concentration of radiation-sensitive color centers in luminescent material.

4. The method of claim 1, wherein each fluorescent light measurement of the one or more fluorescent light measurements is a corrected fluorescent light measurement that is based on one or more diffuse reflection measurements for the fluorescent nuclear track detector performed with illumination light having a third wavelength that is different from the first and second wavelength.

5. The method of claim 4, wherein the one or more diffuse reflection measurements are performed using image acquisition based on diffuse reflection contrast using the illumination light having the third wavelength.

6. The method of claim 5, wherein the image acquisition for the one or more diffuse reflection measurements is performed with the same imaging camera used for image acquisition for plurality of fluorescent light measurements.

7. The method of claim 1, wherein the radiation dose measurement is determined based on an average intensity of one or more images produced by confocal laser scanning of the fluorescent nuclear track detector with the laser and measuring radiation-induced fluorescence from the luminescent material.

8. The method of claim 1, wherein the radiation dose measurement is determined based on a power spectrum integral of one or more images produced by confocal laser scanning of the fluorescent nuclear track detector with the laser and measuring radiation-induced fluorescence from the luminescent material.

9. The method of claim 1, wherein the luminescent material comprises aluminum oxide.

10. The method of claim 9, wherein the luminescent material comprises $Al_2O_3$:C,Mg, wherein the radiation dose measurement is based on one or more "red fluorescent" light measurements produced by confocal laser scanning fluorescent imaging of the fluorescent nuclear track detector using excitation light of the first wavelength from a red laser, and wherein the adjustment of the radiation dose measurements is based on a plurality of green fluorescence contrast images produced by illuminating the fluorescent nuclear track detector with blue excitation light of the second wavelength.

11. The method of claim 10, wherein each fluorescent light measurement of the one or more fluorescent light measurements is a corrected fluorescent light measurement that is based on one or more diffuse reflection measurements for the fluorescent nuclear track detector, and wherein the one or more diffuse reflection measurements are based on one or more diffuse reflection contrast images based on NIR diffuse reflected light produced by illuminating the fluorescent nuclear track detector with NIR illumination light having a third wavelength that is different from the first and second wavelength.

12. The method of claim 11, wherein NIR illumination light and the NIR diffuse reflected light each having a wavelength between 800 and 1000 nm.

13. The method of claim 10, wherein the red laser has a wavelength between 610 and 660 nm.

14. The method of claim 10, wherein the "red fluorescent" light has a wavelength between 680 and 850 nm.

15. The method of claim 10, wherein the blue excitation light has wavelength between 410 and 470 nm.

16. The method of claim 10, wherein the green fluorescence contrast images are generated by green fluorescent light having a wavelength between 470 and 570 nm.

17. The method of claim 1, wherein step (b) comprises displaying the one or more respective calibrated radiation dose measurements to the user.

18. The method of claim 1, wherein step (b) comprises saving the one or more respective calibrated radiation dose measurements to a storage medium.

* * * * *